(12) United States Patent
Umemoto et al.

(10) Patent No.: US 7,541,492 B2
(45) Date of Patent: Jun. 2, 2009

(54) PERFLUOROALKANESULFONAMIDE COMPOUNDS

(75) Inventors: Teruo Umemoto, Denver, CO (US); Masaki Matsui, Susono (JP)

(73) Assignee: Toyota Jidosha Kabushiki Kaisha (JP)

( * ) Notice: Subject to any disclaimer, the term of this patent is extended or adjusted under 35 U.S.C. 154(b) by 298 days.

(21) Appl. No.: 11/258,214

(22) Filed: Oct. 26, 2005

(65) Prior Publication Data

US 2007/0093678 A1 Apr. 26, 2007

(51) Int. Cl.
*C07C 303/00* (2006.01)
(52) U.S. Cl. ...................................................... 564/96
(58) Field of Classification Search ................... 564/96
See application file for complete search history.

(56) References Cited

U.S. PATENT DOCUMENTS 6,534,682 B1 * 3/2003 Hilarius et al. .............. 564/404
6,582,849 B1 * 6/2003 Heider et al. ................ 429/188
6,911,297 B2 * 6/2005 Brzozowy et al. ......... 430/270.1

FOREIGN PATENT DOCUMENTS

| JP | 11-297355 | 10/1999 |
|----|-----------|---------|
| JP | 2003-243028 | 8/2003 |
| JP | 2004-043407 | 2/2004 |

* cited by examiner

*Primary Examiner*—Jafar Parsa
*Assistant Examiner*—Chukwuma O Nwaonicha
(74) *Attorney, Agent, or Firm*—Finnegan, Henderson, Farabow, Garrett & Dunner, LLP

(57) ABSTRACT

The present invention provides compounds represented by the formula $Y^+ {}^-N(SO_2R^f)(CF_3)$. Such a compound can be manufactured through a reaction between $M^+ {}^-N(SO_2R^f)(CF_3)$ and $Y^+ {}^-B$. The present invention also provides compounds represented by the formula $Y^+ {}^-N(SO_2R^f)(CN)$. Such a compound can be manufactured through a reaction between $M^+ {}^-N(SO_2R^f)(CN)$ and $Y^+ {}^-B$. $R^f$ in the above formulae is a perfluoroalkyl group. $Y^+$ is an organic or inorganic cation. $^-B$ is an organic or inorganic anion. $M^+$ is an alkali metal cation or a silver cation.

9 Claims, 1 Drawing Sheet

PERFLUOROALKANESULFONAMIDE COMPOUNDS

BACKGROUND OF THE INVENTION

1. Field of the Invention

The present invention relates to compounds having an anion with a structure in which a perfluoroalkanesulfonyl group and another substituent are bonded to a nitrogen atom, and a method of manufacturing the same. Such a compound can be used, for example, as an electrolyte in any of various electrical storage devices.

2. Description of the Related Art

Bis(trifluoromethanesulfonyl)imide anion ($^-N(SO_2CF_3)_2$, hereinafter referred to as 'TFSI') is known as an anion able to form a salt that exhibits a liquid form in an ambient temperature range (hereinafter sometimes referred to as an 'ambient temperature molten salt' or an 'ionic liquid'). A typical example of an ambient temperature molten salt having this anion is the salt between a 1-ethyl-3-methylimidazolium cation and TFSI.

In Japanese Patent Application Laid-open No. 2004-43407, ionic liquids comprising a compound having an anion with a structure in which two perfluoroalkanesulfonyl groups having different substituents are bonded to a nitrogen atom are described. Other technical documents relating to ionic liquids (ambient temperature molten salts) having an anion with a structure in which two perfluoroalkanesulfonyl groups are bonded to a nitrogen atom are Japanese Patent Application Laid-open No. 2003-243028 and Japanese Patent Application Laid-open No. 11-297355. Japanese Patent Application Laid-open No. 2003-201272 describes onium salts having an amide anion with a structure in which a perfluoroalkanesulfonyl group (e.g. $SO_2CF_3$) and a perfluoroalkanecarbonyl group (e.g. $COCF_3$) are bonded to a nitrogen atom.

In Journal of Enzyme Inhibition Vol. 14 (1999) pp. 289-306, there is description relating to the synthesis of an N-cyanoperfluoroalkanesulfonamide ($RSO_2NHCN$, wherein R is $CF_3$, $n$-$C_4F_9$ or $n$-$C_8F_{17}$). For example, as a method of synthesizing N-cyanotrifluoromethanesulfonamide ($CF_3SO_2NHCN$), a method is described in which cyanamide and triflic acid anhydride (trifluoromethanesulfonic acid anhydride) are suspended in acetone, and triethylamine is instilled in. However, with this method, the triflic acid anhydride and the acetone solvent may react with one another. In actual fact, according to a re-examination carried out by the present inventors, the intended compound N-cyanotrifluoromethanesulfonamide could not be obtained using the above method.

SUMMARY OF THE INVENTION

It is an object of the present invention to provide novel compounds having an anion with a structure in which a perfluoroalkanesulfonyl group and another substituent are bonded to a nitrogen atom. It is another object to provide a suitable method of manufacturing such compounds. It is another object to provide novel compounds related to the process of manufacturing such compounds.

One invention disclosed here relates to a method of manufacturing a compound (perfluoroalkanesulfonamide compound) represented by the formula (1)

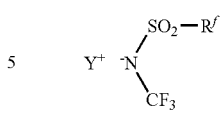
(1)

wherein $R^f$ is any selected from perfluoroalkyl groups having 1 to 4 carbon atoms, and $Y^+$ is any selected from organic and inorganic cations.

This method comprises preparing a first compound represented by the formula (2)

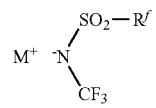
(2)

wherein $R^f$ is any selected from perfluoroalkyl groups having 1 to 4 carbon atoms, and is the same as the perfluoroalkyl group selected in formula (1), and $M^+$ is any selected from alkali metal cations and a silver cation.

The manufacturing method further comprises preparing a second compound represented by the formula (3)

$$Y^{+-}B \qquad (3)$$

wherein $Y^+$ is any selected from organic and inorganic cations, and is the same as the cation selected in formula (1), and $^-B$ is any selected from organic and inorganic anions.

The manufacturing method further comprises reacting the first compound with the second compound to produce the compound represented by formula (1).

Here, 'perfluoroalkyl group' means an alkyl group in which all of the hydrogen atoms have been substituted with fluorine atoms. In the present specification, any organic group in which all of the hydrogen atoms have been substituted with fluorine atoms may be represented by appending 'perfluoro' to the name of the organic group. Moreover, such organic groups in which all of the hydrogen atoms have been substituted with fluorine atoms are sometimes referred to generically as 'perfluoro groups'.

The method disclosed here can be applied to the manufacture of a compound in which $R^f$ in formula (1) is a perfluoroalkyl group. Typically, the method is applied to the manufacture of a compound in which $R^f$ is a perfluoroalkyl group having 1 to 4 carbon atoms.

$Y^+$ in formula (1) is a monovalent cation. This $Y^+$ may be an inorganic cation. For example, $Y^+$ may be any inorganic cation selected from a proton ($H^+$), $NH_4^+$, a hydroxonium ion ($H_3O^+$), an alkali metal (e.g. lithium (Li), sodium (Na), potassium (K), rubidium (Rb) or cesium (Cs)) cation, a transition metal (e.g. silver (Ag), copper (Cu) or gold (Au)) cation, and so on. Alternatively, $Y^+$ may be an organic cation. For example, $Y^+$ may be a monovalent organic cation (that is, a cation of organic compound; likewise hereinafter) containing at least one element selected from nitrogen (N), sulfur (S), oxygen (O) and phosphorus (P). $Y^+$ may also be an organic cation containing at least one element having a lone electron pair in a neutral state other than the above elements. For example, $Y^+$ may be an any organic cation selected from the group consisting of an imidazolium ion (this refers to a cation having an imidazole skeleton; likewise hereinafter), a thiazolium ion, an oxazolium ion, an iso-oxazolium ion, a triazolium ion, a pyridinium ion, a pyridazinium ion, a pyrimidinium ion, a pyrazinium ion, an ammonium ion, a phosphonium ion and a sulfonium ion, each of the above being substituted or unsubstituted. The method disclosed here can be preferably applied to the manufacture of a compound in which $Y^+$ in formula (1) is such an organic cation or inorganic cation.

As the first compound represented by formula (2), a compound in which $M^+$ in formula (2) is an alkali metal cation or a silver cation can be used. Examples of alkali metal cations are $Li^+$, $Na^+$, $K^+$, $Rb^+$ and $Cs^+$. It is preferable to use a compound in which $M^+$ in formula (2) is a silver cation $Ag^+$).

In one preferable embodiment of the method disclosed here, a compound in which $^-B$ in formula (3) is a halide ion is used as the second compound. For example, a salt between a fluoride ion ($F^-$), a chloride ion ($Cl^-$), a bromide ion ($Br^-$) or an iodide ion ($I^-$) and a cation ($Y^+$) corresponding to the structure of the target compound (the perfluoroalkanesulfonamide compound represented by formula (1)) can be preferably used as the second compound.

The first compound may, for example, be one prepared by reacting a compound represented by the formula (4):

$$R^fSO_2N=CX_2 \qquad (4)$$

wherein $R^f$ is any selected from perfluoroalkyl groups having 1 to 4 carbon atoms, and is the same as the perfluoroalkyl group selected in formula (2), and X is any selected from halogen atoms; with a metal fluoride (e.g. AgF) represented by the formula (5)

$$M^+\text{-}F \qquad (5)$$

wherein $M^+$ is any selected from alkali metal cations and a silver cation, and is the same as $M^+$ selected in formula (2).

The preparation of the first compound in this way may, for example, comprise reacting the compound represented by formula (4) with the metal fluoride represented by formula (5) to obtain a product containing the first compound. Moreover, this preparation may comprise making an acid act on the product to produce a compound represented by the formula (6) from the first compound contained in the product

(6)

wherein $R^f$ is any selected from perfluoroalkyl groups having 1 to 4 carbon atoms, and is the same as the perfluoroalkyl group selected in formula (2).

Furthermore, this preparation may comprise reacting the compound represented by formula (6) with the metal fluoride represented by formula (5) (e.g. silver fluoride) to produce the first compound.

The method disclosed here may further comprise preparing the compound represented by formula (4) by reacting a compound represented by the formula (7):

$$R^fSO_2NCO \qquad (7)$$

wherein $R^f$ is any selected from perfluoroalkyl groups having 1 to 4 carbon atoms, and is the same as the perfluoroalkyl group selected in formula (4); with a phosphorus pentahalide. The compound represented by formula (7) can be manufactured using a known method (see, for example, Journal of Fluorine Chemistry, Vol. 4 (1974) pp. 83-98).

The present invention provides compounds (perfluoroalkanesulfonamide compounds) represented by the formula (8).

(8)

Here, $R^f$ in formula (8) is any selected from perfluoroalkyl groups having 1 to 4 carbon atoms. For example, $R^f$ may be a trifluoromethyl group ($CF_3$) or a pentafluoroethyl group ($CF_2CF_3$).

$Y^+$ in formula (8) is any selected from organic and inorganic cations. For example, $Y^+$ may be an organic cation. In one preferable embodiment of the compound disclosed here, $Y^+$ in formula (8) is an organic ammonium cation. This organic ammonium cation may be either aliphatic or aromatic. A preferable example of the ammonium cation is a substituted or unsubstituted imidazolium cation. Other preferable examples of the ammonium cation are ammonium cations having four mutually independent aliphatic groups, and ammonium cations having four aliphatic groups at least two of which are linked together.

The compound represented by formula (8) can, for example, be suitably manufactured by applying any of the methods described above.

The present invention further provides compounds represented by the formulae (9) to (11). These compounds are each related to a compound represented by formula (1) or (8). Compounds represented by formulae (9) to (11) can, for example, be suitably used in the process of manufacturing compounds represented by formula (1) or (8).

That is, the present invention provides compounds represented by the formula (9).

(9)

Here, $R^f$ is any selected from perfluoroalkyl groups having 1 to 4 carbon atoms. $M^+$ is any selected from alkali metal cations (e.g. any one selected from the group consisting of $Li^+$, $Na^+$, $K^+$, $Rb^+$ and $Cs^+$) and a silver cation. $M^+$ is preferably a silver cation $Ag^+$).

Moreover, the present invention provides compounds represented by the formula (10).

$$R^fSO_2N=CX_2 \qquad (10)$$

Here, $R^f$ is any selected from perfluoroalkyl groups having 1 to 4 carbon atoms. X is any selected from halogen atoms. Examples of halogen atoms are a fluorine atom, a chlorine atom, a bromine atom and an iodine atom.

Moreover, the present invention provides compounds represented by the formula (11).

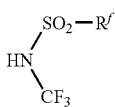
(11)

Here, $R^f$ is any selected from perfluoroalkyl groups having 1 to 4 carbon atoms.

Note that the anionic part of each compound represented by formula (1), (2), (8) or (9) will principally have the following resonance structures (A), (B) and (C).

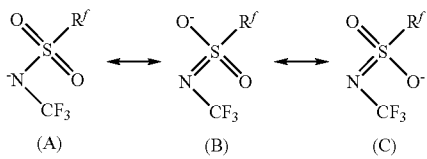

Consequently, whichever of these resonance structures (A), (B) and (C) is used to represent the anionic part, the compound is the same.

Moreover, the compound represented by formula (6) or (11) is the same as a compound of formula (1) or (8) in which $Y^+$ is a proton ($H^+$).

Another invention disclosed here relates to a method of manufacturing a compound (perfluoroalkanesulfonamide compound) represented by the formula (12)

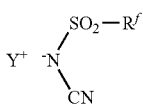
(12)

wherein $R^f$ is any selected from perfluoroalkyl groups having 1 to 4 carbon atoms, and $Y^+$ is any selected from organic and inorganic cations.

This method comprises preparing a first compound represented by the formula (13)

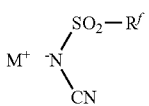
(13)

wherein $R^f$ is any selected from perfluoroalkyl groups having 1 to 4 carbon atoms, and is the same as the perfluoroalkyl group selected in formula (12), and $M^+$ is any selected from alkali metal cations and a silver cation.

The manufacturing method further comprises preparing a second compound represented by the formula (14)

$$Y^+ {}^- B \tag{14}$$

wherein $Y^+$ is any selected from organic and inorganic cations, and is the same as the cation selected in formula (12), and $^-B$ is any selected from organic and inorganic anions.

The manufacturing method further comprises reacting the first compound with the second compound to produce the compound represented by formula (12).

The method disclosed here can be applied to the manufacture of a compound in which $R^f$ in formula (12) is a perfluoroalkyl group. Typically, the method is applied to the manufacture of a compound in which $R^f$ is a perfluoroalkyl group having 1 to 4 carbon atoms.

$Y^+$ in formula (12) is a monovalent cation. This $Y^+$ may be an inorganic cation. For example, $Y^+$ may be any inorganic cation selected from $H^+$, $NH_4^+$, $H_3O^+$, an alkali metal (e.g. Li, Na, K, Rb or Cs) cation, a transition metal (e.g. Ag, Cu or Au) cation, and so on. Alternatively, $Y^+$ may be an organic cation. For example, $Y^+$ may be a monovalent organic cation containing at least one element selected from N, S, O and P. $Y^+$ may also be an organic cation containing at least one element having a lone electron pair in a neutral state other than the above elements. For example, $Y^+$ may be an any organic cation selected from the group consisting of an imidazolium ion, a thiazolium ion, an oxazolium ion, an iso-oxazolium ion, a triazolium ion, a pyridinium ion, a pyridazinium ion, a pyrimidinium ion, a pyrazinium ion, an ammonium ion, a phosphonium ion and a sulfonium ion, each of the above being substituted or unsubstituted. The method disclosed here can be preferably applied to the manufacture of a compound in which $Y^+$ in formula (12) is such a cation.

As the above-mentioned first compound, a compound in which $M^+$ in formula (13) is an alkali metal cation or a silver cation ($Ag^+$) is used. The alkali metal cation may be any selected from the group consisting of $Li^+$, $Na^+$, $K^+$, $Rb^{+0}$ and $Cs^+$. In one preferable embodiment of the method disclosed here, a compound in which $M^+$ in formula (13) is a silver cation is used as the first compound.

In one preferable embodiment of the method disclosed here, a compound in which B in formula (14) is a halide ion is used as the second compound. For example, a salt between a fluoride ion ($F^-$), a chloride ion ($Cl^-$), a bromide ion ($Br^-$) or an iodide ion ($I^-$) and a cation ($Y^+$) corresponding to the structure of the target compound (the perfluoroalkanesulfonamide compound represented by formula (12)) can be preferably used as the second compound.

The first compound used in the method disclosed here may, for example, be one prepared by reacting a compound represented by the formula (15):

wherein $R^f$ is any selected from perfluoroalkyl groups having 1 to 4 carbon atoms, and is the same as the perfluoroalkyl group selected in formula (13), and $R^1$, $R^2$ and $R^3$ are each independently any selected from alkyl groups having 1 to 4 carbon atoms; with a metal fluoride represented by the formula (16)

wherein $M^+$ is any selected from alkali metal cations and a silver cation, and is the same as $M^+$ selected in formula (13). Examples of the metal fluoride represented by formula (16) are alkali metal fluorides and silver fluoride ($Ag^{+-}F$, i.e. AgF). Examples of alkali metal fluorides are $Li^{+-}F$ (LiF), $Na^{+-}F$ (NaF), $K^{+-}F$ (KF), $Rb^{+-}F$ (RbF) and $Cs^{+-}F$ (CsF).

The method disclosed here may further comprise preparing the compound represented by formula (15) by reacting a compound represented by the formula (17):

wherein $R^f$ is any selected from perfluoroalkyl groups having 1 to 4 carbon atoms, and is the same as the perfluoroalkyl group selected in formula (15), $R^1$, $R^2$ and $R^3$ are each independently any selected from alkyl groups having 1 to 4 carbon atoms, and are the same as those selected in formula (15), and M⁺ is any selected from alkali metal cations and a silver cation; with a cyanogen halide. As the cyanogen halide, FCN, ClCN, BrCN (cyanogen bromide) or ICN can be used. From the viewpoint of the yield, it is preferable to use ClCN, BrCN or ICN.

The first compound may alternatively be manufactured through the following method. That is, the first compound represented by formula (13) may be one prepared by reacting a compound represented by the formula (20):

$$[R^fSO_2NH]^-(M^1)^+ \quad (20)$$

wherein $R^f$ is any selected from perfluoroalkyl groups having 1 to 4 carbon atoms, and is the same as the perfluoroalkyl group selected in formula (13), and $(M^1)^+$ is any selected from alkali metal cations and a silver cation;

with a cyanogen halide, in the presence of a compound represented by the formula (18) or (19)

$$[(M^2)^+]_2 CO_3^{2-} \quad (18)$$

$$(M^2)^+HCO_3^- \quad (19)$$

wherein $(M2)^+$ in formula (18) or (19) is any selected from alkali metal cations and a silver cation.

Typically, at least one of $(M2)^+$ in formula (18) or (19) and $(M^1)^+$ in formula (20) is the same as M⁺ in formula (13). $(M^1)^+$ and $(M2)^+$ may be the same as one another or different. From the viewpoint of a product of higher purity being readily obtained, it is preferable for $(M^1)^+$ and $(M^2)^+$ to be the same cation.

Yet another invention disclosed here relates to another method of manufacturing a compound (perfluoroalkanesulfonamide compound) represented by the formula (12)

wherein $R^f$ is any selected from perfluoroalkyl groups having 1 to 4 carbon atoms, and Y⁺ is any selected from organic and inorganic cations.

This manufacturing method comprises preparing a first compound represented by the formula (15)

$$R^fSO_2N(CN)(SiR^1R^2R^3) \quad (15)$$

wherein $R^f$ is any selected from perfluoroalkyl groups having 1 to 4 carbon atoms, and is the same as the perfluoroalkyl group selected in formula (12), and $R^1$, $R^2$ and $R^3$ are each independently any selected from alkyl groups having 1 to 4 carbon atoms.

The manufacturing method further comprises preparing a second compound represented by the formula (14)

$$Y^+{}^-B \quad (14)$$

wherein Y⁺ is any selected from organic and inorganic cations, and is the same as the cation selected in formula (12), and ⁻B is any selected from organic and inorganic anions.

The manufacturing method further comprises reacting the first compound with the second compound to produce the compound represented by formula (12).

Y⁺ in formula (14) may be the same as that described above for Y⁺ in formula (12). Moreover, ³¹B in formula (14) is preferably a halide ion.

The present invention also provides compounds (perfluoroalkanesulfonamide compounds) represented by the formulae (21).

Here, $R^f$ in formula (21) is any selected from perfluoroalkyl groups having 1 to 4 carbon atoms. For example, $R^f$ may be a trifluoromethyl group ($CF_3$) or a pentafluoroethyl group ($CF_2CF_3$).

$(Y^1)^+$ in formula (21) is any selected from organic and inorganic cations except H⁺. For example, $(Y^1)^+$ may be an organic cation. In one preferable embodiment of the compound disclosed here, $(Y^1)^+$ in formula (21) is an organic ammonium cation. This organic ammonium cation may be either aliphatic or aromatic. A preferable example of the ammonium cation is a substituted or unsubstituted imidazolium cation. Other preferable examples of the ammonium cation are ammonium cations having four mutually independent aliphatic groups, and ammonium cations having four aliphatic groups at least two of which are linked together.

The compound represented by formula (21) can, for example, be suitably manufactured by applying any of the methods described above.

The present invention provides compounds represented by the formula (23). Such a compound can, for example, be suitably used in the process of manufacturing a compound represented by formula (12) or (21).

Here, $R^f$ in formula (23) is any selected from perfluoroalkyl groups having 1 to 4 carbon atoms. M⁺ is any selected from alkali metal cations and a silver cation.

The present invention also provides compounds represented by the formula (15). Such a compound can, for example, be suitably used in the process of manufacturing a compound represented by formula (21) or (23).

$$R^fSO_2N(CN)(SiR^1R^2R^3) \quad (15)$$

Here, $R^f$ in formula (15) is any selected from perfluoroalkyl groups having 1 to 4 carbon atoms. $R^1$, $R^2$ and $R^3$ are each independently any selected from alkyl groups having 1 to 4 carbon atoms. Examples of alkyl groups having 1 to 4 carbon atoms are —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)CH_2CH_3$ and —$CH_2C(CH_3)_3$. Of these particularly preferable ones are —$CH_3$ and —$CH_2CH_3$.

A compound represented by formula (15) may comprise several structural isomers. Examples of these structural isomers are the three (15a), (15b) and (15c) shown below.

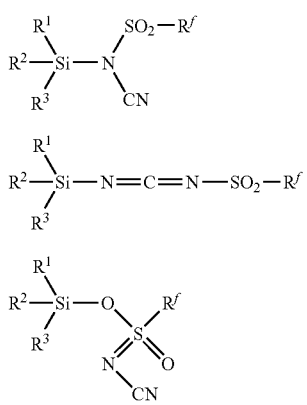

A compound represented by formula (15) may, for example, be a mixture of the three structural isomers represented by formulae (15a), (15b) and (15c), or may be a mixture of any two selected from these three structural isomers, or may be any one of these three structural isomers. That is, a composition constituted substantially from the three structural isomers represented by formulae (15a), (15b) and (15c), a composition constituted substantially from any two selected from these three structural isomers, and a composition constituted substantially from any one of these three structural isomers are all included in the invention disclosed here.

Moreover, the anionic part of each compound represented by formula (12), (13), (21) or (23) will principally have the following resonance structures (D), (E), (F) and (G).

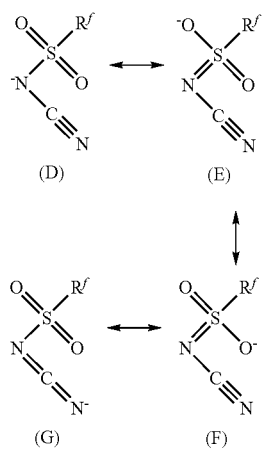

Consequently, whichever of these resonance structures (D), (E), (F) and (G) is used to represent the anionic part, the compound is the same.

The present invention provides compounds (salts) comprising an anionic component represented by the formula $^-N(SO_2R^f)(CF_3)$ (hereinafter the anion represented by this formula is sometimes referred to as '$R^fSTI$') and an organic or inorganic cation ($Y^+$). Moreover, the present invention provides compounds (salts) comprising an anionic component represented by the formula $^-N(SO_2R^f)(CN)$ (hereinafter the anion represented by this formula is sometimes referred to as '$R^fSC$') and an organic or inorganic cation ($Y^+$). Such a compound (in particular, a compound in which $Y^+$ is an organic cation) may be a salt that exhibits a liquid form at least at approximately 30° C. (typically at approximately 30° C. and lower temperatures). Moreover, such a compound may be a salt that exhibits a liquid form at least at approximately 20° C. Furthermore, such a compound may be a salt that exhibits a liquid form at least at approximately 0° C. Preferable examples of the compounds disclosed here are salts that comprise $R^fSTI$ or $R^fSC$ and an organic cation and exhibit a liquid form in a temperature range around ambient temperature (an ambient temperature range). Here, 'ambient temperature' is the temperature of an environment that is neither heated nor cooled, and an 'ambient temperature range' is, for example, a temperature range having an upper limit of approximately 80° C. (typically approximately 60° C., sometimes approximately 40° C.), and a lower limit of approximately −20° C. (typically approximately 0° C., sometimes approximately 20° C.). The salts disclosed here may be salts at least part of which exhibits a liquid form (a molten state) over at least part of such a temperature range. For example, a salt at least part (preferably the whole) of which is able to maintain a liquid form (molten state) over a temperature range of at least approximately 20 to 40° C. (more preferably approximately 0 to 60° C., yet more preferably approximately −20 to +80° C.) is preferable.

The present invention may provide ionic liquids comprising a salt which comprises $R^fSTI$ or $R^fSC$ and an organic or inorganic cation (typically an organic cation). An ionic liquid comprises as a principal component thereof a salt between $R^fSTI$ or $R^fSC$ and an organic or inorganic cation is preferable.

Here, 'ionic liquid' means an ionic compound that is able to maintain a liquid state over an ambient temperature range as described above. An ionic liquid that exhibits a liquid form at least at approximately 25° C. is preferable.

Specific examples of the ionic liquids disclosed here are ionic liquids each constituted primarily from a compound (salt) in which the anionic component is represented by the formula $^-N(SO_2CF_3)(CF_3)$ (hereinafter the anion represented by this formula is sometimes referred to as 'TTI'), and the cationic component is any selected from 1-ethyl-3-methylimidazolium, 1-ethyl-2,3-dimethylimidazolium and tetrabutylammonium. Another specific example of the ionic liquids disclosed here is an ionic liquid constituted primarily from a compound (salt) in which the anionic component is represented by the formula $^-N(SO_2CF_2CF_3)(CF_3)$, and the cationic component is 1-ethyl-3-methylimidazolium.

Yet other specific examples of the ionic liquids disclosed here are ionic liquids each constituted primarily from a compound (salt) in which the anionic component is represented by the formula $^-N(SO_2CF_3)(CN)$ (hereinafter the anion represented by this formula is sometimes referred to as 'TC'), and the cationic component is any selected from 1-ethyl-3-methylimidazolium, 1,2-dimethyl-3-ethylimidazolium, 1,2-dimethyl-3-propylimidazolium, N-methyl-N-propylpyrrolidinium, and the cation represented by the formula (22).

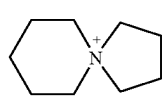

The following are included in the invention disclosed through this specification.

[1] An electrolyte comprising one or two or more kinds of salts selected from salts between $R^fSTI$ or $R^fSC$ and a cation (an organic cation or an inorganic cation). A preferable example of such an electrolyte is an electrolyte comprising one or two or more kinds of salts selected from salts between R$^f$STI or R$^f$SC and an organic cation. In one preferable embodiment of the electrolyte disclosed here, the electrolyte comprises as a principal component thereof a salt between R$^f$STI or R$^f$SC and an organic cation, the salt being in a liquid form (a molten state) over at least part of an ambient temperature range as described above. For example, an electrolyte comprising as a principal component thereof a salt able to maintain a liquid state at least at approximately 30° C. (more preferably approximately 20° C., yet more preferably approximately 0° C., particularly preferably −20° C.) is preferable.

In addition to the one or two or more kinds of salts selected from salts between R$^f$STI or R$^f$SC and an organic cation, the electrolyte disclosed here may comprise one or two or more kinds of salts selected from salts between an inorganic or organic anion and a lithium cation (lithium salts). Such a lithium salt may be a salt between R$^f$STI or R$^f$SC and a lithium cation. An electrolyte that is a composition comprising the lithium salt and exhibits a liquid form in an ambient temperature range is preferable. For example, an electrolyte that exhibits a liquid form at least at approximately 30° C. (more preferably approximately 20° C., yet more preferably approximately 0° C., particularly preferably −20° C.) is preferable. One preferable embodiment of such an electrolyte is a liquid electrolyte in which one or two or more selected from salts between R$^f$STI and a lithium cation and salts between R$^f$SC and a lithium cation (supporting salt(s)) is/are dissolved in a medium that is substantially constituted from one or two or more selected from salts between R$^f$STI or R$^f$SC and an organic cation and exhibits a liquid form in an ambient temperature range.

[2] An electrical storage device having an electrolyte as described above. Here 'electrical storage device' is a concept encompassing both electrochemical cells or batteries (including primary cells and secondary cells; examples include lithium ion batteries and nickel hydrogen batteries) and capacitors (examples include electric double layer capacitors). Such an electrical storage device may be, for example, a lithium ion secondary battery containing an electrolyte as described above. In one preferable embodiment of such a cell, the cell contains an electrolyte that exhibits a liquid form in an ambient temperature range. For example, it is preferable for the cell having an electrolyte that exhibits a liquid form at least at approximately 30° C. (preferably approximately 20° C., more preferably approximately 0° C., particularly preferably −20° C.).

[3] An ion-conducting material comprising one or two or more kinds of salts selected from salts between R$^f$STI or R$^f$SC and a cation (an organic cation or an inorganic cation). An ion-conducting material exhibiting a liquid form in an ambient temperature range is preferable. Such an ion-conducting material can be used, for example, as a constituent element of an electrical storage device or any of various other electrochemical devices. Moreover, such an ion-conducting material can be used as an electrolyte of a photochemical cell such as a solar cell or a power generating device such as a fuel cell, or a constituent thereof.

[4] A medium comprising one or two or more kinds of salts selected from salts between R$^f$STI or R$^f$SC and a cation (an organic cation or an inorganic cation). A medium that is substantially constituted from one or two or more selected from such salts and is able to maintain a liquid form in an ambient temperature range is preferable. Such a medium can be preferably used in any of various applications as a nonflammable solvent, a nonvolatile solvent or the like. For example, such a medium may be useful as a solvent for dissolving a supporting salt such as a lithium salt in an non-aqueous electrolyte of a battery such as a lithium ion secondary battery (i.e. as a medium for an electrolyte).

DETAILED DESCRIPTION OF THE INVENTION

Figure 1:
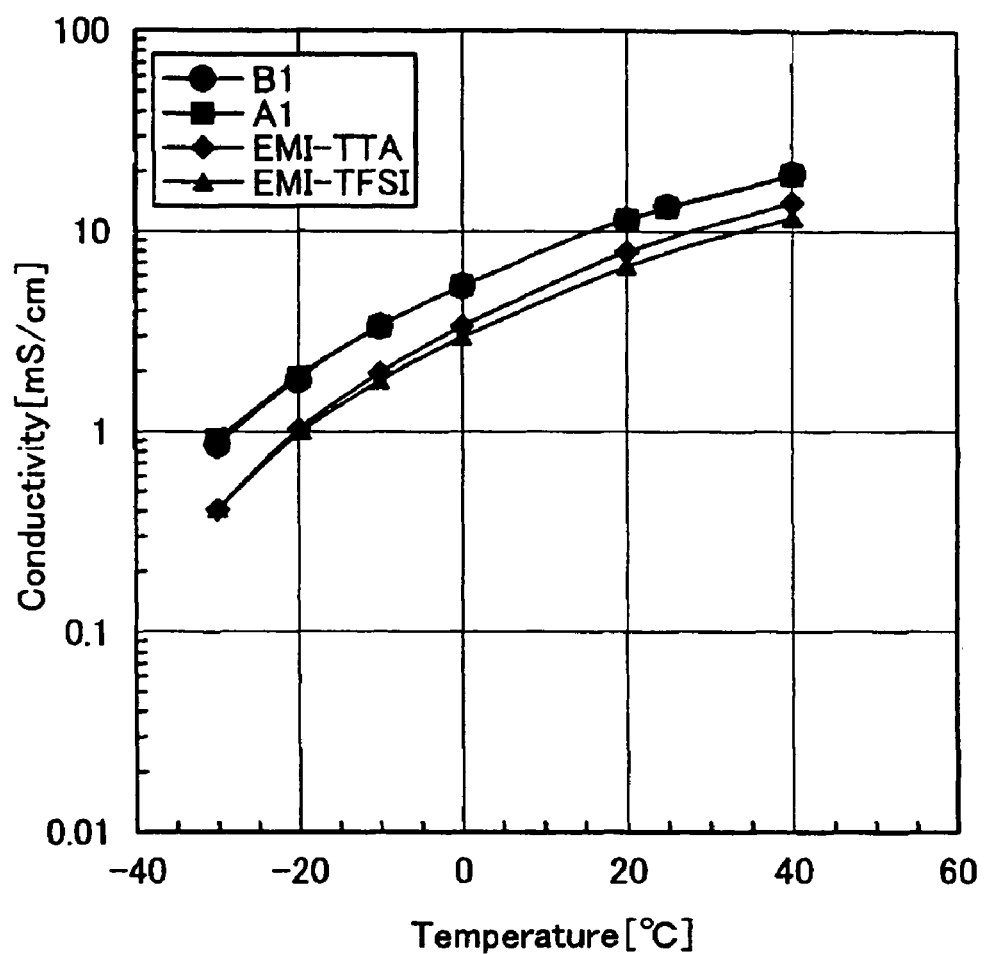
FIG. 1 is a graph showing the relationship between ionic conductivity and temperature for various ionic liquids.

Following is a detailed description of preferable embodiments of the present invention. Note that technical matters that are required for carrying out the present invention but are not particularly mentioned in the present specification are matters of design variation that could be apprehended by a person skilled in the art based on prior art. The present invention can be carried out based on the technical details disclosed in the present specification and common general technical knowledge in the field in question.

<Anionic Component>

A compound disclosed here contains an anionic component represented by the formula $^-$N(SO$_2$R$^f$)(CF$_3$). This anionic component (R$^f$STI) has a structure in which a sulfonyl group (—SO$_2$—) and a trifluoromethyl group (—CF$_3$) are each bonded to a nitrogen atom (N).

Another compound disclosed here contains an anionic component represented by the formula $^-$N(SO$_2$R$^f$)(CN). This anionic component (R$^f$SC) has a structure in which a sulfonyl group (—SO$_2$—) and a cyano group (—CN) are each bonded to a nitrogen atom (N).

Each of R$^f$STI and R$^f$SC is an anion having a perfluoroalkyl group (R$^f$) bonded to the above-mentioned sulfonyl group. The perfluoroalkyl group as R$^f$ may be an open chain, or may form a cyclic structure. Here, unless otherwise stated, 'open chain' is a concept including both unbranched open chains (straight chain) and branched open chains (branched chain). An anion in which R$^f$ is an open chain (straight chain or branched chain) perfluoroalkyl group is preferable. That is, an anion having a structure in which a perfluoroalkanesulfonyl group is bonded to the nitrogen atom is preferable.

The total number of carbon atoms contained in R$^f$ is preferably 1 to 4. Preferable examples of R$^f$ are straight chain or branched chain (more preferably straight chain) perfluoroalkyl groups having this number of carbon atoms. Specific examples of such perfluoroalkyl groups are —CF$_3$, —CF$_2$CF$_3$, —CF$_2$CF$_2$CF$_3$, —CF(CF$_3$)CF$_3$, —CF$_2$CF$_2$CF$_2$CF$_3$, —CF(CF$_3$)CF$_2$CF$_3$ and —CF$_2$CF(CF$_3$)CF$_3$. Of these, particularly preferable ones are —CF$_3$ and —CF$_2$CF$_3$.

<Cationic Component>

The cation (Y$^+$, counter ion) paired with R$^f$STI or R$^f$SC to form a salt may be an inorganic cation, or may be an organic cation. Y$^+$ may be a monovalent organic cation containing at least one element selected from nitrogen (N), sulfur (S), oxygen (O) and phosphorus (P). For example, Y$^+$ may be a cation having a structure in which one or a plurality of organic groups is/are bonded to at least one such element (N, S, O or P) contained in the cation. A preferable example of such an organic group is an open chain (e.g. straight chain) alkyl group having 1 to 10 (preferably 1 to 6) carbon atoms and optionally containing an ether linkage. Moreover, the cationic component may also be an organic cation containing at least one element having a lone electron pair in a neutral state other than N, S, O or P. [Imidazolium ions]

A preferable example of $Y^+$ is an imidazolium ion represented by the formula (C1).

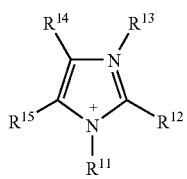

Here, $R^{11}$ to $R^{15}$ in formula (C1) can each be independently selected from a hydrogen atom, halogen atoms, and organic groups having 1 to 10 carbon atoms. Two or more of $R^{11}$ to $R^{15}$ may be linked together to form a cyclic structure. In this case, these groups may form the cyclic structure with an oxygen atom interposed therebetween, or without an oxygen atom interposed therebetween. Typically, at least one of the nitrogen atoms in the imidazole ring has an organic group having 1 to 10 carbon atoms thereon. In other words, at least one of $R^{11}$ and $R^{13}$ (preferably both) is an organic group having 1 to 10 carbon atoms.

In the case that any of $R^{11}$ to $R^{15}$ is a halogen atom, this halogen atom may be selected from the group consisting of, Cl, Br and I. Moreover, in the case that any of $R^{11}$ to $R^{15}$ is an organic group as described above, this organic group may be a hydrocarbon group optionally containing an ether linkage. The hydrocarbon group may be open chain, or may form a cyclic structure. Moreover, the hydrocarbon group may be either saturated or unsaturated. In the case that the hydrocarbon group forms a cyclic structure, the ring may be aromatic or non-aromatic. Some or all of the hydrogen atoms in the hydrocarbon group may be substituted with halogen atoms (e.g. one or a plurality of halogen atoms selected from the group consisting of F, Cl, Br and I). An example of such a halogen-substituted hydrocarbon group is a perfluoroalkyl group optionally containing an ether linkage.

In a preferable example of the cation represented by formula (C1), $R^{11}$ to $R^{15}$ are each independently selected from a hydrogen atom and substituted or unsubstituted alkyl groups having 1 to 10 carbon atoms. The alkyl groups may be open chain, or may form a cyclic structure. Open chain alkyl groups are preferable, with straight chain alkyl groups being particularly preferable. In the case that an alkyl group has substituents (i.e. is a substituted alkyl group), the substituents may be halogen atoms. For example, the substituents may be one or a plurality of halogen atoms selected from the group consisting of F, Cl, Br and I (preferably fluorine atoms). In one preferable embodiment, $R^{11}$ to $R^{15}$ are each independently selected from a hydrogen atom and substituted or unsubstituted (preferably unsubstituted) open chain alkyl groups having 1 to 4 carbon atoms. Examples of such alkyl groups are —CH₃, —CH₂CH₃, —CH₂CH₂CH₃, —CH₂CH₂CH₂CH₃, —CH(CH₃)CH₃, —CH(CH₃)CH₂CH₃, —CH₂CH(CH₃)CH₃ and —C(CH₃)₂CH₃. Of these, particularly preferable ones are —CH₃, —CH₂CH₃, —CH₂CH₂CH₃ and —CH₂CH₂CH₂CH₃.

In a preferable example of the cation represented by formula (C1), the groups out of $R^{11}$ to $R^{15}$ that are bonded to a nitrogen atom in the imidazole ring (i.e. $R^{11}$ and $R^{13}$) are each independently selected from alkyl groups having 1 to 4 carbon atoms. Moreover, the groups that are bonded to a carbon atom in the imidazole ring (i.e. $R^{12}$, $R^{14}$ and $R^{15}$) are each independently selected from a hydrogen atom and alkyl groups having 1 to 4 carbon atoms. For example, the cation may be an imidazolium ion in which the groups bonded to the 1-position, the 2-position and the 3-position of the imidazole ring ($R^{11}$, $R^{12}$ and $R^{13}$) are each an alkyl group having 1 to 4 carbon atoms. Alternatively, the cation may be an imidazolium ion in which the groups bonded to the 1-position, the 2-position and the 3-position of the imidazole ring ($R^{11}$, $R^{12}$ and $R^{13}$) are each an alkyl group having 1 to 4 carbon atoms, and moreover one or both of the groups bonded to the 4-position and the 5-position ($R^{14}$, $R^{15}$) is/are an alkyl group having 1 to 4 carbon atoms.

Specific examples of the cation represented by formula (C1) include dialkyl imidazolium ions such as a 1,3-dimethylimidazolium ion, a 1,3-diethylimidazolium ion, a 1,3-dipropylimidazolium ion, a 1-ethyl-3-methylimidazolium ion, a 1-methyl-3-propylimidazolium ion, a 1-methyl-3-butylimidazolium ion, and a 1-isopropyl-3-propylimidazolium ion; trialkyl imidazolium ions such as a 1,2,3-trimethylimidazolium ion, a 1,2,3-triethylimidazolium ion, a 1-ethyl-2,3-dimethylimidazolium ion, a 1,2-dimethyl-3-propylimidazolium ion, and a 2-ethyl-1,3-dimethylimidazolium ion; tetraalkyl imidazolium ions such as a 1,2,3,4-tetramethylimidazolium ion, a 1,2,3,4-tetraethylimidazolium ion, and a 2-ethyl-1,3,4-trimethylimidazolium ion; and pentaalkyl imidazolium ions such as a 1,2,3,4,5-pentamethylimidazolium ion, and a 1-ethyl-2,3,4,5-tetramethylimidazolium ion.

[Pyridinium Ions]

Another preferable example of $Y^+$ is a pyridinium ion represented by the formula (C2).

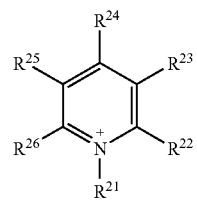

Here, $R^{21}$ to $R^{26}$ in formula (C2) can each be independently selected from a hydrogen atom, halogen atoms (e.g. F, Cl, Br, I), and organic groups having 1 to 10 carbon atoms. Two or more of $R^{21}$ to $R^{26}$ may be linked together to form a cyclic structure. In this case, these groups may form the cyclic structure with an oxygen atom interposed therebetween, or without an oxygen atom interposed therebetween. Typically, the nitrogen atom in the pyridine ring has an organic group having 1 to 10 carbon atoms thereon. In other words, $R^{21}$ is an organic group having 1 to 10 carbon atoms.

In the case that any of $R^{21}$ to $R^{26}$ is an organic group, this organic group may be as with $R^{11}$ to $R^{15}$ described above. For example, the organic group may be a hydrocarbon group optionally containing an ether linkage. Moreover, the hydrocarbon group may be substituted or unsubstituted. Moreover, the hydrocarbon group may be open chain, or may have a cyclic structure. In the case that any of $R^{21}$ to $R^{26}$ is a hydrocarbon group, a preferable example thereof is an alkyl group having 1 to 10 (more preferably 1 to 4) carbon atoms that is substituted or unsubstituted and optionally contains an ether linkage. An open chain alkyl group is preferable. Moreover, an unsubstituted alkyl group is preferable. Examples of particularly preferable alkyl groups are —CH₃, —CH₂CH₃, —CH₂CH₂CH₃ and —CH₂CH₂CH₂CH₃.

In one preferable embodiment, the group bonded to the nitrogen atom in the pyridine ring ($R^{21}$) is an alkyl group having 1 to 10 (more preferably 1 to 4) carbon atoms. Moreover, $R^{22}$ to $R^{26}$ are each independently selected from a hydrogen atom and alkyl groups having 1 to 10 (more preferably 1 to 4) carbon atoms. Typically, each of $R^{22}$ to $R^{26}$ is a hydrogen atom. Specific examples of the cation represented by formula (C2) include an N-methylpyridinium ion, an N-ethylpyridinium ion, an N-propylpyridinium ion, an N-isopropylpyridinium ion, and an N-butylpyridinium ion.

[Oxazolium Ions]

Another preferable example of $Y^+$ is an oxazolium ion represented by the formula (C3).

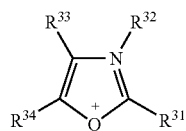

(C3)

Here, $R^{31}$ to $R^{34}$ in formula (C3) can each be independently selected from a hydrogen atom, halogen atoms (e.g. F, Cl, Br, I), and organic groups having 1 to 10 carbon atoms. Two or more of $R^{31}$ to $R^{34}$ may be linked together to form a cyclic structure, either with an oxygen atom interposed therebetween or without an oxygen atom interposed therebetween. Typically, the nitrogen atom in the oxazole ring has an organic group having 1 to 10 carbon atoms thereon. In other words, $R^{32}$ is an organic group having 1 to 10 carbon atoms.

In the case that any of $R^{31}$ to $R^{34}$ is an organic group, this organic group may be as with $R^{11}$ to $R^{15}$ described above. For example, the organic group may be a hydrocarbon group optionally containing an ether linkage. Moreover, the hydrocarbon group may be substituted or unsubstituted. Moreover, the hydrocarbon group may be open chain, or may have a cyclic structure. In the case that any of $R^{31}$ to $R^{34}$ is a hydrocarbon group, a preferable example thereof is an alkyl group having 1 to 10 (more preferably 1 to 4) carbon atoms that is substituted or unsubstituted and optionally contains an ether linkage. An open chain alkyl group is preferable. Moreover, an unsubstituted alkyl group is preferable. Examples of particularly preferable alkyl groups are —$CH_3$, —$CH_2CH_3$, —$CH_2CH_2CH_3$ and —$CH_2CH_2CH_2CH_3$.

In one preferable embodiment, the group bonded to the nitrogen atom in the oxazole ring ($R^{32}$) is an alkyl group having 1 to 10 (more preferably 1 to 4) carbon atoms. Moreover, $R^{31}$, $R^{33}$, and $R^{34}$ are each independently selected from a hydrogen atom and alkyl groups having 1 to 10 (more preferably 1 to 4) carbon atoms. Typically, each of $R^{31}$, $R^{33}$, and $R^{34}$ is a hydrogen atom. Specific examples of the cation represented by formula (C3) include an N-methyloxazolium ion, an N-ethyloxazolium ion, an N-propyloxazolium ion, and an N-butyloxazolium ion.

[Ammonium Ions]

Another preferable example of $Y^+$ is an ammonium ion represented by the formula (C4).

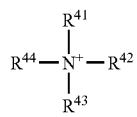

(C4)

Here, $R^{41}$ to $R^{44}$ in formula (C4) can each be independently selected from a hydrogen atom and organic groups having 1 to 10 carbon atoms. Typically, at least one of $R^{41}$ to $R^{44}$ is selected from organic groups having 1 to 10 carbon atoms, and the others are each independently selected from a hydrogen atom and organic groups having 1 to 10 carbon atoms. It is preferable for at least two (more preferably at least three) of $R^{41}$ to $R^{44}$ to be an organic group having 1 to 10 carbon atoms. Typically, each of $R^{41}$ to $R^{44}$ is an organic group having 1 to 10 carbon atoms. Two or more of $R^{41}$ to R may be linked together to form a non-aromatic ring, either with an oxygen atom interposed therebetween or without an oxygen atom interposed therebetween.

In the case that any of $R^{41}$ to $R^{44}$ is an organic group, this organic group may be as with $R^{11}$ to $R^{15}$ described above. For example, the organic group may be a hydrocarbon group optionally containing an ether linkage. Moreover, the hydrocarbon group may be substituted or unsubstituted. Moreover, the hydrocarbon group may be open chain, or may have a cyclic structure. In the case that any of $R^{41}$ to $R^{44}$ is a hydrocarbon group, a preferable example thereof is an alkyl group or alkenyl group having 1 to 10 carbon atoms that is substituted or unsubstituted (preferably unsubstituted) and optionally contains an ether linkage. Preferable examples of $R^{41}$ to $R^{44}$ are open chain (preferably straight chain) alkyl groups having 1 to 4 carbon atoms such as —$CH_3$, —$CH_2CH_3$, —$CH_2CH_2CH_3$ and —$CH_2CH_2CH_2CH_3$. Other preferable examples of $R^{41}$ to $R^{44}$ are open chain (preferably straight chain) alkyl groups having 2 to 10 (preferably 2 to 5) carbon atoms containing one or a plurality of ether linkages.

Specific examples of the cation represented by formula (C4) include tetraalkylammonium ions in which $R^{41}$ to $R^{44}$ are each the same alkyl group such as a tetramethylammonium ion, a tetraethylammonium ion, a tetrapropylammonium ion, and a tetrabutylammonium ion. Other examples are tetraalkylammonium ions in which $R^{41}$ to $R^{44}$ are two or more kinds of alkyl groups such as an ethyltrimethylammonium ion, a triethylmethylammonium ion, a diethyldimethylammonium ion, a trimethylpropylammonium ion, a triethylpropylammonium ion, a trimethylisopropylammonium ion, a triethylisopropylammonium ion, a dimethyldipropylammonium ion, a butyltrimethylammonium ion, and a tributylmethylammonium ion. Yet other examples are ammonium ions in which at least one of $R^{41}$ to $R^{44}$ is an alkenyl group and the others are alkyl group such as a vinyltrimethylammonium ion, and an allyltrimethylammonium ion. Yet other examples are ammonium ions in which at least one of $R^{41}$ to $R^{44}$ is an alkyl group containing an ether linkage (an alkylether group) and the others are alkyl groups such as a 2-methoxyethyl-trimethylammonium ion, a 2-ethoxyethyl-trimethylammonium ion, and a 2-methoxyethyl-triethylammonium ion.

Two or more of $R^{41}$ to $R^{44}$ may be linked together to form a non-aromatic ring. This non-aromatic ring may be an aliphatic ring containing the nitrogen atom. For example, the non-aromatic ring may be an aliphatic 5-membered ring containing a nitrogen atom (a pyrrolidine ring), an aliphatic 6-membered ring containing a nitrogen atom (a piperidine ring), and so on. The carbon atoms in the ring may or may not have substituents thereon. In the case of having substituents, each of the substituents may be a halogen atom (e.g. F, Cl, Br or I; preferably F), an alkyl group having 1 to 4 carbon atoms, such an alkyl group in which some or all of the hydrogen atoms have been substituted with halogen atoms, and so on. The cation represented by formula (C4) may be an ammonium ion having a structure in which two of $R^{41}$ to $R^{44}$ (e.g. $R^{41}$ and $R^{42}$) are linked together to form an unsubstituted pyrrolidine ring or piperidine ring (i.e. a pyrrolidinium ion or a piperidinium ion). The remainder of $R^{41}$ to $R^{44}$ may each be an alkyl group or alkenyl group having 1 to 10 (preferably 1 to 4) carbon atoms that is substituted or unsubstituted (preferably unsubstituted) and optionally contains an ether linkage.

A preferable example of such a $Y^+$ represented by formula (C4) is a cation represented by the formula (C5).

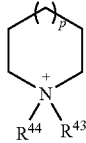

(C5)

Here, $R^{43}$ and $R^{44}$ in formula (C5) are each independently a substituted (e.g. halogenated) or unsubstituted alkyl group having 1 to 10 carbon atoms and optionally containing an ether linkage, and p is a chemical bond or an alkylene group having one carbon atom.

In the case that p is a chemical bond, this cation is a pyrrolidinium ion, and in the case that p is an alkylene group having one carbon atom (i.e. a methylene group), this cation is a piperidinium ion. $R^{43}$ and $R^{44}$ are each independently a substituted or unsubstituted alkyl group having 1 to 10 carbon atoms and optionally containing an ether linkage. Preferable examples of groups that can be selected as $R^{43}$ and $R^{44}$ include open chain (preferably straight chain) alkyl groups having 1 to 4 carbon atoms, and open chain (preferably straight chain) alkyl groups having 2 to 10 (more preferably 2 to 5) carbon atoms containing one or a plurality of ether linkages.

Alternatively, $R^{43}$ and $R^{44}$ in formula (C5) may be linked together to form a cyclic structure. In this case, these groups may form the cyclic structure with an oxygen atom interposed therebetween, or without an oxygen atom interposed therebetween. The ring may be aromatic or non-aromatic (aliphatic). For example, $Y^+$ may be a cation having a structure in which $R^{43}$ and $R^{44}$ in formula (C5) are linked together to form an aliphatic 5-membered ring (a pyrrolidinium ring) or an aliphatic 6-membered ring (a piperidinium ring). Moreover, $Y^+$ may also be a cation having a structure in which $R^{43}$ and $R^{44}$ are linked together to form an aliphatic 4-membered ring or an aliphatic 7-membered ring.

In one preferable embodiment, one or both of $R^{43}$ and $R^{44}$ in formula (C5) is/are an alkyl group containing an ether linkage. This alkyl group containing an ether linkage may be, for example, a group represented by the formula (C5a).

—$R^{61}$—O(—$R^{62}$—O)$_m$—$R^{63}$ (C5a)

Here, $R^{61}$ and $R^{62}$ in formula (C5a) are each independently a substituted or unsubstituted alkylene group having 1 to 3 carbon atoms. $R^{63}$ is a substituted or unsubstituted alkyl group having 1 to 5 carbon atoms. Examples of substituents that $R^{61}$ to $R^{63}$ may possess are halogen atoms (e.g. F, Cl, Br, I). It is preferable for each of $R^{61}$ to $R^{63}$ to be unsubstituted. It is preferable for each of $R^{61}$ to $R^{63}$ to be open chain (preferably straight chain). The group represented by formula (C5a) may contain one (m=0) to three (m=2) ether linkages. m is preferably 0 or 1. In the case that there are a plurality of $R^{62}$s in formula (C5a), these $R^{62}$s may be the same as one another or different.

Specific examples of the cation represented by formula (C5) are dialkylpyrrolidinium ions and dialkylpiperidinium ions such as an N,N-dimethylpyrrolidinium ion, an N-ethyl-N-methylpyrrolidinium ion, an N-methyl-N-propylpyrrolidinium ion, an N-butyl-N-methylpyrrolidinium ion, an N,N-dimethylpiperidinium ion, an N-ethyl-N-methylpiperidinium ion, and an N-methyl-N-propylpiperidinium ion. Moreover, the cation may be a pyrrolidinium ion or piperidinium ion in which one of $R^{43}$ and $R^{44}$ is any alkylether group selected from $CH_3OCH_2CH_2$—, $CH_3CH_2OCH_2CH_2$—, $CH_3OCH_2CH_2OCH_2CH_2$— and $CH_3CH_2OCH_2CH_2OCH_2CH_2$—, and the other is any alkyl group selected from —$CH_3$, —$CH_2CH_3$, —$CH_2CH_2CH_3$ and —$CH_2CH_2CH_2CH_3$. The cation may also be a pyrrolidinium ion or piperidinium ion in which $R^{43}$ and $R^{44}$ are both independently any alkylether group selected from $CH_3OCH_2CH_2$—, $CH_3CH_2OCH_2CH_2$—, $CH_3OCH_2CH_2OCH_2CH_2$— and $CH_3CH_2OCH_2CH_2OCH_2CH_2$—. Moreover, examples of a cyclic structure formed through $R^{43}$ and $R^{44}$ being linked together include —$(CH_2)_3$—, —$(CH_2)_4$—, —$(CH_2)_5$—, —$(CH_2)_6$— and —$CH_2CH_2OCH_2CH_2$—.

[Sulfonium Ions]

Another preferable example of $Y^+$ is a sulfonium ion represented by the formula (C6).

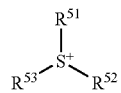

(C6)

Here, $R^{51}$ to $R^{53}$ in formula (C6) can each be independently selected from a hydrogen atom and organic groups having 1 to 10 carbon atoms. Typically, at least one of $R^{51}$ to $R^{53}$ is selected from organic groups having 1 to 10 carbon atoms, and the others are each independently selected from a hydrogen atom and organic groups having 1 to 10 carbon atoms. It is preferable for at least two of $R^{51}$ to $R^{53}$ to be an organic group having 1 to 10 carbon atoms. Typically, each of $R^{51}$ to $R^{53}$ is an organic group having 1 to 10 carbon atoms. Two or more of $R^{51}$ to $R^{53}$ may be linked together to form a non-aromatic ring, either with an oxygen atom interposed therebetween or without an oxygen atom interposed therebetween.

In the case that any of $R^{51}$ to $R^{53}$ is an organic group, this organic group may be as with $R^{11}$ to $R^{15}$ described above. For example, the organic group may be a hydrocarbon group optionally containing an ether linkage. Moreover, the hydrocarbon group may be substituted or unsubstituted. Moreover, the hydrocarbon group may be open chain, or may have a cyclic structure. In the case that any of $R^{51}$ to $R^{53}$ is a hydrocarbon group, a preferable example thereof is an alkyl group having 1 to 10 (preferably 1 to 4) carbon atoms that is substituted or unsubstituted and optionally contains an ether linkage. An open chain alkyl group is preferable. Moreover, an unsubstituted alkyl group is preferable. Examples of particularly preferable alkyl groups are —$CH_3$, —$CH_2CH_3$, —$CH_2CH_2CH_3$ and —$CH_2CH_2CH_2CH_3$. Specific examples of the cation represented by formula (C6) include trialkylsulfonium ions such as a trimethylsulfonium ion, a triethylsulfonium ion, a tripropylsulfonium ion, a tributylsulfonium ion, a dimethylethylsulfonium ion, a diethylmethylsulfonium ion, and a dimethylpropylsulfonium ion.

[Other Organic Cations]

$Y^+$ may also be a thiazolium ion, an iso-oxazolium ion, a triazolium ion, a pyridazinium ion, a pyrimidinium ion, or a pyrazinium ion. With these ions, typically, a nitrogen atom in the heterocyclic ring (at least one of the nitrogen atoms in the case of a ring containing two or more nitrogen atoms) has an organic group having 1 to 10 carbon atoms as a substituent thereon. This organic group may be, for example, an open chain alkyl group having 1 to 10 (preferably 1 to 4) carbon atoms and optionally containing an ether linkage. On the other hand, other atoms in the heterocyclic ring (e.g. carbon atoms) may or may not have substituents thereon. In the case of having substituents, each of the substituents may be selected from halogen atoms (e.g. F, Cl, Br or I; preferably F), and organic groups having 1 to 10 carbon atoms. Such an organic group having 1 to 10 carbon atoms may be, for example, an open chain alkyl group having 1 to 10 (preferably 1 to 4) carbon atoms and optionally containing an ether linkage.

Moreover, $Y^+$ may be a phosphonium cation having a structure in which the nitrogen atom (N) in formula (C4) is replaced with a phosphorus atom (P). Specific examples of such a phosphonium cation are tetraalkylphosphonium ions such as a tetramethylphosphonium ion, a tetraethylphosphonium ion, a tetrapropylphosphonium ion, a tetrabutylphosphonium ion, a trimethylethylphosphonium ion, and a triethylmethylphosphonium ion. Moreover, two or more of $R^{41}$ to $R^{44}$ may be linked together to form a non-aromatic ring (typically an aliphatic 5-membered or 6-membered ring containing the phosphorus atom).

A salt between any of the organic cations ($Y^+$) described above and $R^f$STI or $R^f$SC may be a salt at least part of which exhibits a liquid form in an ambient temperature range as described above (such a salt may be referred to as an 'ambient temperature molten salt', a 'room temperature molten salt', an 'ionic liquid' or the like). In a preferable embodiment of the salt disclosed here, the salt exhibits a liquid form at least at approximately 30° C. (more preferably approximately 20° C., yet more preferably approximately 0° C.). A salt at least part (preferably the whole) of which is able to maintain a liquid form (molten state) over a temperature range of at least approximately 20 to 40° C. (more preferably approximately 0 to 60° C., yet more preferably approximately −20 to +80° C.) is preferable.

The trifluoromethyl group (—$CF_3$) or cyano group (—CN) bonded to the nitrogen atom in the above anionic component ($R^f$STI or $R^f$SC) is a substituent having a relatively low molecular weight. The molecular weight of such a —$CF_3$ group or —CN group is, for example, clearly lower than that of a substituent such as a trifluoromethanesulfonyl group (—$SO_2CF_3$) or a trifluoromethanecarbonyl group (—$COCF_3$). $R^f$STI or $R^f$SC may thus be an anion having a lower molecular weight than an anion having a structure in which the —$CF_3$ group of $R^f$STI or the —CN group of $R^f$SC is replaced with, for example, an —$SO_2CF_3$ group (a bis-sulfonyl type anion). The salt between a particular cation and $R^f$STI or $R^f$SC may thus have a lower melting point than the salt between this cation and the above bis-sulfonyl type anion, and moreover may have a lower viscosity, and furthermore may have a better ionic conductivity (or may exhibit a desirable ionic conductivity for practical use in a lower temperature region). Such a salt may be useful as a constituent element of an electrical storage device or other type of electrochemical device. For example, it may be that such a salt can be suitably used as a constituent of an electrolyte exhibiting a liquid form in an ambient temperature range (e.g. an electrolyte for any of various electrical storage devices such as a lithium ion secondary battery). A salt between $R^f$STI or $R^f$SC and an organic cation can be preferably used as a solvent (medium) for dissolving a supporting electrolyte in such an electrolyte.

[Inorganic Cations]

The cation ($Y^+$) paired with $R^f$STI or $R^f$SC to form the salt may also be an inorganic cation. For example, $Y^+$ may be an alkali metal ion. Examples of alkali metal ions are a lithium ion, a sodium ion, a potassium ion, a rubidium ion, and a cesium ion. It may be that a salt between such an inorganic cation and $R^f$STI or $R^f$SC can, for example, be suitably used as a constituent of an electrolyte as described later (typically, a supporting electrolyte that supplies an inorganic cation to the electrolyte). Other examples of inorganic cations that can be selected as $Y^+$ are transition metal ions such as a silver ion ($Ag^+$), a copper ion ($Cu^+$) or a gold ion ($Au^+$). For example, a salt between $R^f$STI or $R^f$SC and a silver ion is suitable as a raw material (intermediate) for manufacturing a salt between $R^f$STI or $R^f$SC and an organic cation or the like. Yet other examples of inorganic cations that can be selected as $Y^+$ include $H^+$, $NH_4^+$ and $H_3O^+$.

<Method of Manufacturing a Salt Between $R^f$STI and a Cation>

A salt between an anion represented by the formula $^-N(SO_2R^f)(CF_3)$ and a cation (i.e. a compound represented by formula (1)) can, for example, be suitably manufactured through a method comprising at least one of steps A1 to A3 described below.

[Step A1]

The isocyanate group of a compound represented by formula (7) $R^fSO_2NCO$ is converted into an —N=$CX_2$ group. This conversion can be suitably realized, for example, through a step including a reaction between the compound represented by formula (7) and a phosphorus pentahalide (hereinafter sometimes referred to as 'step A1'). Through this reaction, a compound represented by formula (4) $R^fSO_2N=CX_2$ can be produced. The compound represented by formula (7) used in the reaction can, for example, be prepared using a method described in a publicly known document (see Journal of Fluorine Chemistry, Vol. 4 (1974) pp. 83-98).

Examples of the phosphorus pentahalide used in this step are $PF_5$, $PCl_5$, $PBr_5$ and $PI_5$. $PCl_5$ and $PBr_5$ are preferable from the viewpoint of economy. Of these, it is particularly preferable to use $PCl^5$. It is generally appropriate to make the amount used of the phosphorus pentahalide be within a range of approximately 0.8 to 5 mol of the phosphorus pentahalide per 1 mol of the $R^fSO_2NCO$. From the viewpoints of economy, yield and so on, the amount used of the phosphorus pentahalide per 1 mol of the $R^fSO_2NCO$ is preferably made to be within a range of approximately 1 to 2 mol, more preferably within a range of approximately 1 to 1.5 mol.

The above reaction can be made to proceed without using a solvent in particular. Alternatively, the reaction may be carried out using an appropriate solvent. As the solvent, for example one or a plurality selected from halocarbons such as dichloromethane, trichloromethane and tetrachloromethane can be used as appropriate. It is preferable to use an aprotic solvent.

The reaction can be made to proceed in a temperature range of, for example, approximately 100 to 250° C. From the viewpoint of improving the yield and so on, it is generally preferable to carry out the reaction in a temperature range of approximately 150 to 220° C.

[Step A2]

The —N=$CX_2$ group of a compound represented by formula (4) is converted into an N-trifluoromethyl group (—$NCF_3$). This conversion can be realized, for example, through a step including a reaction between the compound represented by formula (4) and a metal fluoride ($M^{+-}F$) represented by formula (5) (hereinafter sometimes referred to as 'step A2'). Through this reaction, a first compound represented by formula (2) $M^{+-}N(SO_2R^f)(CF_3)$, i.e. a salt between $R^fSTI$ and a metal cation ($M^+$), can be produced. The compound represented by formula (4) used in this reaction can, for example, be prepared using a method including step A1 described above.

In the case that X is a halogen atom other than a fluorine atom, the molar ratio between the $R^fSO_2N=CX_2$ and the $M^+F$ used when carrying out this reaction ($R^fSO_2N=CX_2:M^{+-}F$) can generally be selected from within a range of 1:2.5 to 1:10. From the viewpoints of economy, yield and so on, this molar ratio is preferably made to be within a range of 1:3 to 1:6, more preferably 1:3 to 1:5. In the case that X is a fluorine atom, the above molar ratio can generally be selected from within a range of 1:0.8 to 1:3. From the viewpoints of economy, yield and so on, this molar ratio is preferably made to be within a range of 1:1 to 1:2, more preferably 1:1 to 1:1.5.

A solvent is not necessarily required in the reaction, but it is generally preferable to use a solvent so that the reaction can be made to proceed more smoothly and with a better yield. As the solvent, for example one or a plurality selected from nitriles such as acetonitrile and propionitrile, ethers such as diethyl ether, ethyl propyl ether, dipropyl ether, diisopropyl ether, dibutyl ether, tetrahydrofuran and dimethoxyethane, ketones such as acetone and methyl ethyl ketone, esters such as methyl formate, ethyl formate, methyl acetate, ethyl acetate and methyl propionate, halocarbons such as dichloromethane, trichloromethane, tetrachloromethane and dichloroethane, and so on can be used as appropriate. A nitrile such as acetonitrile or propionitrile can be preferably used.

The reaction can be made to proceed in a temperature range of, for example, approximately −30 to 150° C. From the viewpoint of improving the yield and so on, it is generally preferable to carry out the reaction in a temperature range of approximately 0 to 120° C. (more preferably approximately room temperature to 100° C.).

As necessary, the product (containing the first compound) obtained through the reaction between the compound represented by formula (4) and the metal fluoride represented by formula (5) may be further subjected to the following processing.

That is, processing is carried out in which an acid is made to act on the product, thus producing a compound represented by formula (6) $R^fSO_2NHCF_3$ from the first compound contained in the product. As the acid, either an inorganic acid or an organic acid can be used. It is generally preferable to use an inorganic acid. Moreover, a so-called strong acid can be preferably used. Preferable examples of the acid used in this processing include hydrogen fluoride (HF), hydrogen chloride (HCl), hydrogen bromide (HBr) and hydrogen iodide (HI). From the viewpoints of economy, handleability and so on, it is particularly preferable to use hydrogen chloride. For example, the reaction can be made to proceed suitably by making hydrogen chloride gas contact the above product.

The amount of the acid used is generally preferably made to be an equimolar amount or an excess amount. Specifically, this amount may generally be selected as appropriate from within a range of 1 to 100 mol per 1 mol of the compound represented by formula (2). From the viewpoint of economy, it is preferable to select this amount from within a range of 1 to 50 mol, more preferably approximately 1 to 20 mol.

A solvent is not necessarily required in the reaction, but it is generally preferable to use a solvent so that the reaction can be made to proceed more smoothly and efficiently. As the solvent used, for example one or a plurality selected from the ethers, nitrites and halocarbons mentioned earlier and so on can be used as appropriate. For example, a halocarbon such as dichloromethane or trichloromethane can be preferably used.

The reaction can be made to proceed in a temperature range of, for example, approximately −30 to +150° C. From the viewpoints of economy, yield and so on, it is generally preferable to carry out the reaction in a temperature range of approximately 0 to 50° C.

Next, processing of reacting the compound produced through the above reaction ($R^fSO_2NHCF_3$) with a metal fluoride is carried out. As a result, the first compound represented by formula (2) can be produced. The molar ratio between the metal fluoride ($M^{+-}F$) and the $R^fSO_2NHCF_3$ used when carrying out this processing ($M^{+-}F: R^fSO_2NHCF_3$) can, for example, be made to be within a range of 1:0.7 to 1:1.5 (preferably 1:0.8 to 1:1.2). It is generally appropriate to make this molar ratio be approximately 1:1.

A solvent is not necessarily required in the reaction, but it is generally preferable to use a solvent so that the reaction can be made to proceed more smoothly and efficiently. As the solvent used, one or a plurality selected from the ethers, nitrites, esters, ketones and halocarbons mentioned earlier and so on can be used as appropriate. For example, a nitrile such as acetonitrile or propionitrile, or an ether such as diethyl ether, ethyl propyl ether, dipropyl ether, diisopropyl ether or dibutyl ether can be preferably used.

The reaction can be made to proceed in a temperature range of, for example, approximately −30 to +100° C. From the viewpoint of improving the yield and so on, it is generally preferable to carry out the reaction in a temperature range of approximately −10 to +50° C.

By carrying out the above processing, for example, a first compound of higher purity can be prepared.

[Step A3]

The cation ($M^+$) of a first compound represented by formula (2) is exchanged to the cation ($Y^+$) in the final target substance (i.e. the compound represented by formula (1)). This cation exchange can be suitably realized through a step including a reaction between the first compound represented by formula (2) and a second compound represented by formula (3) (hereinafter sometimes referred to as 'step A3'). The first compound used in this reaction can, for example, be prepared using a method including step A2 described above.

As the second compound, a salt between a cation ($Y^+$) the same as the cation in the final target substance and an organic or inorganic anion ($B^-$) can be used. Such a second compound will either be a readily procurable known substance, or else can be easily synthesized through a known method. Preferable examples of the anion ($B^-$) in the second compound are anions of halogens such as fluorine (F), chlorine (Cl), bromine (Br) or iodine (I) (i.e. halide ions). For example, a salt between a fluoride ion ($F^-$), a chloride ion ($Cl^-$), a bromide ion ($Br^-$) or an iodide ion ($I^-$) and $Y^+$ can be preferably used as the second compound. In the case that $B^-$ is a fluorine anion ($F^-$), this $F^-$ may be in the form of a composite salt with HF (i.e. $(F^-)(HF)_n$, wherein n is, for example, an integer from 1 to 10). Other examples of second compounds that can be used in this step are salts between $Y^+$ and an anion ($B^-$) such as a carboxylate anion such as $^-OCOCH_3$, $^-OCOCF_3$, $^-OCOC_2H_5$ or $^-OCOC_6H_5$, a sulfonate anion such as $^-OSO_2CH_3$, $^-OSO_2CF_3$, $^-OSO_2C_2H_5$, $^-OSO_2C_6H_5$, $^-OSO_2C_6H_4CH_3$, $^-OSO_2F$ or $^-OSO_2Cl$, or a sulfate anion such as $^-OSO_2OH$ (or $^{-HSO_4}$), $^-OSO_2OCH_3$ or $^-OSO_2OC_2H_5$.

It is generally appropriate for the amount used of the compound represented by formula (2) to be selected from within a range of 0.5 to 1.5 mol per 1 mol of the compound represented by formula (3) ($Y^{+-}B$). From a viewpoint of obtaining the target substance with a good yield, the amount used of the compound represented by formula (2) is preferably made to be within a range of 0.7 to 1.2 mol per 1 mol of the $Y^{+-}B$. From the viewpoint of economy, this amount is more preferably made to be within a range of 0.8 to 1.1 mol.

A solvent is not necessarily required in the reaction, but it is generally preferable to use a solvent so that the reaction can be made to proceed more smoothly and with a better yield. As the solvent used, one or a plurality selected from the ethers, nitrites, esters, ketones and halocarbons mentioned earlier, water and so on can be used as appropriate. For example, a nitrile such as acetonitrile or propionitrile can be preferably used.

The reaction can be made to proceed in a temperature range of, for example, −30 to +100° C. From the viewpoint of improving the yield and so on, it is generally preferable to carry out the reaction in a temperature range of 0 to 50° C.

<Method of Manufacturing a Salt Between $R^fSC$ and a Cation>

A salt between an anion represented by the formula $^-N(SO_2R)(CN)$ and a cation (i.e. a compound represented by formula (12)) can, for example, be suitably manufactured through a method including at least one of steps B1 to B5 described below.

[Step B1]

A compound represented by formula (17) $[R^fSO_2N(SiR^1R^2R^3)]^-M^+$ is reacted with a cyanogen halide, thus obtaining a compound represented by formula (15) $R^fSO_2(CN)(SiR^1R^2R^3)$. This step (hereinafter sometimes referred to as 'step B1') can typically be represented by the following reaction formula.

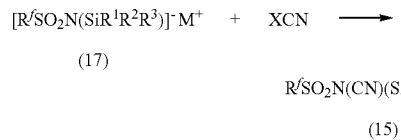

Here, as the compound represented by formula (17), a compound having an $R^f$ group the same as the $R^f$ group in the compound represented by formula (12) (i.e. the final target substance) can be used. A compound in which $R^f$ in formula (17) is a perfluoroalkyl group having 1 to 4 carbon atoms can be synthesized following a known method (see, for example, Inorganic Chemistry, Vol. 32 (1993) pp. 5007-5010). $R^1$, $R^2$ and $R^3$ in the compound represented by formula (17) are each independently an alkyl group having 1 to 4 carbon atoms (preferably a methyl group or an ethyl group). Moreover, $M^+$ in the compound represented by formula (17) is an alkali metal cation or a silver cation. From the viewpoint of economy, it is preferable to use a compound in which $M^+$ is an alkali metal cation.

Examples of cyanogen halides (XCN) that can be used in the present step are FCN, ClCN, BRCN and ICN. Of these, it is preferable to use ClCN, BrCN or ICN.

A solvent is not necessarily required in the reaction, but it is preferable to use a solvent so that the reaction can be carried out with a good yield. As the solvent used, for example one or a plurality selected from nitriles such as acetonitrile and propionitrile, ethers such as diethyl ether, ethyl propyl ether, dipropyl ether, diisopropyl ether and dibutyl ether, halocarbons such as dichloromethane, trichloromethane, tetrachloromethane and dichloroethane, and so on can be used as appropriate. Out of these, it is particularly preferable to use a nitrile.

The reaction can be made to proceed in a temperature range of, for example, −30 to +120° C. From the viewpoint of improving the yield and so on, it is generally preferable to carry out the reaction in a temperature range of 0 to 100° C.

It is generally appropriate for the amount used of the compound represented by formula (17) when carrying out the reaction to be selected from within a range of 0.5 to 1.5 mol per 1 mol of the cyanogen halide (XCN). From the viewpoint of obtaining the target substance with a good yield, the amount used of the compound represented by formula (17) is preferably made to be within a range of 0.7 to 1.2 mol per 1 mol of the cyanogen halide. From the viewpoint of economy, this amount is more preferably made to be within a range of 0.9 to 1.1 mol.

[Step B2]

A compound represented by formula (15) $R^fSO_2N(CN)(SiR^1R^2R^3)$ is reacted with a metal fluoride ($M^{+-}F$), thus obtaining a compound represented by formula (23) $[R^fSO_2NCN]^-M^+$. This step (hereinafter sometimes referred to as 'step B2') can typically be represented by the following reaction formula.

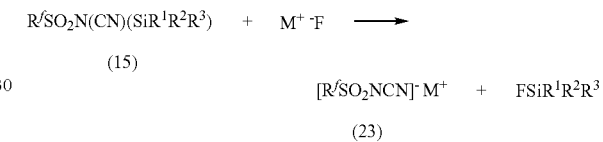

The compound represented by formula (15) used in this reaction can, for example, be prepared using a method including step B1 described above. Examples of metal fluorides ($M^{+-}F$) that can be used in this step are alkali metal fluorides and silver fluoride (AgF). Specific examples of alkali metal fluorides are LiF, NaF, KF, RbF and CsF.

A solvent is not necessarily required in the reaction, but it is preferable to use a solvent so that the reaction can be carried out efficiently. As the solvent used, for example one or a plurality selected from nitriles such as acetonitrile and propionitrile, halocarbons such as dichloromethane, trichloromethane, tetrachloromethane and dichloroethane, ethers such as diethyl ether, ethyl propyl ether, dipropyl ether, diisopropyl ether and dibutyl ether, esters such as methyl acetate and ethyl acetate, and so on can be used as appropriate. Out of these, it is particularly preferable to use a nitrile.

The reaction can be made to proceed in a temperature range of, for example, −80 to +120° C. From the viewpoint of improving the yield and so on, it is generally preferable to carry out the reaction in a temperature range of −10 to +80° C.

It is generally appropriate for the amount used of the compound represented by formula (15) when carrying out the reaction to be selected from within a range of 0.5 to 1.5 mol per 1 mol of the metal fluoride ($M^{+-}F$). From the viewpoint of obtaining the target substance with a good yield, the amount used of the compound represented by formula (15) is preferably made to be within a range of 0.7 to 1.2 mol per 1 mol of the metal fluoride. From the viewpoint of economy, this amount is more preferably made to be within a range of 0.8 to 1.1 mol.

[Step B3]

A compound represented by formula (20) $[R^fSO_2NH]^-M^1)^+$ is reacted with a cyanogen halide (XCN) in the presence of a carbonate ($[(M^2)^+]_2CO_3^{2-}$) or hydrogencarbonate ($(M2)^+HCO_3^-$), thus obtaining a compound represented by formula (23) $[R^fSO_2NCN]^-M^+$. This is another example of a step that can be used to synthesize a compound represented by formula (23). This step (hereinafter sometimes referred to as 'step B3') can typically be represented by the following reaction formula.

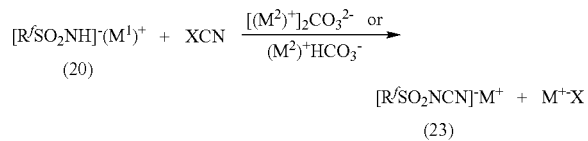

Here, $(M^1)^+$, $(M^2)^+$ and $M^+$ are any selected from alkali metal cations and a silver cation. Examples of alkali metal cations are $Li^+$, $Na^+$, $K^+$, $Rb^+$ and $Cs^+$. At least one of $(M^1)^+$ and $(M^2)^+$ is the same as $M^+$ in the compound represented by formula (23) that is the product of the present step. From the viewpoint of a product of higher purity being readily obtained, it is preferable for both $(M^1)^+$ and $(M^2)^+$ to be the same as $M^+$.

The compound represented by formula (20) used in the present step can easily be synthesized following a known method (see, for example, Inorganic Chemistry, Vol. 32 (1993) pp. 5007-5010). For example, the compound represented by formula (20) can be obtained by making an alkali metal hydroxide, an alkali metal alkoxide, silver oxide or the like act on a compound represented by the formula $R^fSO_2NH_2$.

Examples of cyanogen halides that can be used in the present step are FCN, ClCN, BrCN and ICN. Of these, it is preferable to use ClCN, BrCN or ICN.

Examples of carbonates $[(M^2)^+]_2CO_3^{2-}$ that can be used in the present step are lithium carbonate, sodium carbonate, potassium carbonate, rubidium carbonate, cesium carbonate and silver carbonate. Moreover, examples of hydrogen carbonates $(M^2)^+HCO_3^-$ that can be used in the present step are lithium hydrogencarbonate, sodium hydrogencarbonate, potassium hydrogencarbonate, rubidium hydrogencarbonate, cesium hydrogencarbonate and silver hydrogencarbonate.

It is generally appropriate for the amount used of the compound represented by formula (20) to be selected from within a range of 0.5 to 1.5 mol per 1 mol of the cyanogen halide. From a viewpoint of obtaining the target substance with a good yield, the amount used of the compound represented by formula (20) is preferably made to be within a range of 0.7 to 1.2 mol per 1 mol of the cyanogen halide. From the viewpoint of economy, this amount is more preferably made to be within a range of 0.8 to 1.1 mol.

In the case of using a carbonate $[(M^2)^+]_2CO_3^{2-}$ in the present step, it is generally appropriate for the amount used thereof to be selected from within a range of 0.4 mol to 5 mol per 1 mol of the cyanogen halide. From the viewpoints of economy and yield, the amount used of the carbonate $[(M^2)^+]_2CO_3^{2-}$ is preferably made to be within a range of 0.5 mol to 3 mol per 1 mol of the cyanogen halide. Moreover, in the case of using a hydrogencarbonate $(M2)^+ HCO_{3-}$ in the present step, it is generally appropriate for the amount used thereof to be selected from within a range of 0.8 mol to 10 mol per 1 mol of the cyanogen halide. From the viewpoints of economy and yield, the amount used of the hydrogencarbonate $(M^2)^+HCO_3^-$ is preferably made to be within a range of 1 to 6 mol per 1 mol of the cyanogen halide.

A solvent is not necessarily required in the reaction, but it is preferable to use a solvent so that the reaction can be carried out efficiently. As the solvent used, for example one or a plurality selected from nitriles such as acetonitrile and propionitrile, halocarbons such as dichloromethane, trichloromethane, tetrachloromethane and dichloroethane, ethers such as diethyl ether, ethyl propyl ether, dipropyl ether, diisopropyl ether and dibutyl ether, esters such as methyl acetate and ethyl acetate, and so on can be used as appropriate. Out of these, it is particularly preferable to use a nitrile.

The reaction can be made to proceed in a temperature range of, for example, $-30$ to $+150°$ C. From the viewpoint of improving the yield and so on, it is generally preferable to carry out the reaction in a temperature range of $-10$ to $+80°$ C.

[Step B4]

A compound represented by formula (23) $[R^fSO_2NCN]^-M^+$ is reacted with a compound represented by formula (14) $Y^{+-}B$, thus obtaining a compound represented by formula (12) $Y^+[R^fSO_2NCN]^-$. This step (hereinafter sometimes referred to as 'step B4') can typically be represented by the following reaction formula.

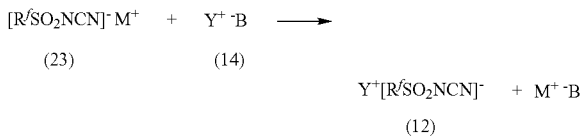

The compound represented by formula (23) used in the present step can, for example, be prepared using a method including step B2 or B3 described above. As the compound represented by formula (14), a compound in which $Y^+$ is an organic or inorganic cation the same as that in the final target compound represented by formula (12) can be used. Here, $^-B$ in formula (14) is an organic or inorganic anion. As the compound represented by formula (14), for example a compound in which $^-B$ is a halide anion ($F^-$, $Cl^-$, $Br^-$ or $I^-$,) can be preferably used. Alternatively, as the compound represented by formula (14) a compound in which $^-B$ is an organic or inorganic anion such as a carboxylate anion such as $^-OCOCH_3$, $^-OCOCF_3$, $^-OCOC_2H_5$ or $^-OCOC_6H_5$, a sulfonate anion such as $^-OSO_2CH_3$, $^-OSO_2CF_3$, $^-OSO_2C_2H_5$, $^-OSO_2C_6H_5$, $^-OSO_2C_6H_4CH_3$, $^-OSO_2F$ or $^{-OSO}{}_2Cl$, or a sulfate anion such as $^{-OSO}{}_2OH$ (or $^-HSO_4$), $^-OSO_2OCH_3$ or $^-OSO_2OC_2H_5$ may be used. In the case that $^-B$ is a fluorine anion ($F^-$), this $F^-$ may be in the form of a composite salt with HF (i.e. $(F^-)(HF)^n$, wherein n is, for example, an integer from 1 to 10).

$R^f$ in formula (23) is any selected from perfluoroalkyl groups having 1 to 4 carbon atoms, and is the same as $R^f$ in the final target substance (i.e. the compound represented by formula (12)).

It is generally appropriate for the amount used of the compound represented by formula (23) to be selected from within a range of 0.5 to 1.5 mol per 1 mol of the $Y^{+-}B$. From a viewpoint of obtaining the target substance with a good yield, the amount used of the compound represented by formula (23) is preferably made to be within a range of 0.7 to 1.2 mol per 1 mol of the $Y^{+-}B$. From the viewpoint of economy, this amount is more preferably made to be within a range of 0.8 to 1.1 mol.

A solvent is not necessarily required in the reaction, but it is preferable to use a solvent so that the reaction can be carried out efficiently. As the solvent used, for example one or a plurality selected from nitriles such as acetonitrile and propionitrile, halocarbons such as dichloromethane, trichloromethane, tetrachloromethane and dichloroethane, ethers such as diethyl ether, ethyl propyl ether, dipropyl ether, diisopropyl ether and dibutyl ether, esters such as methyl acetate and ethyl acetate, ketones such as acetone and methyl ethyl ketone, water and so on can be used as appropriate.

The reaction can be made to proceed in a temperature range of, for example, −30 to +100° C. From the viewpoint of improving the yield and so on, it is generally preferable to carry out the reaction in a temperature range of 0 to 50° C.

[Step B5]

A compound represented by formula (15) R$^f$SO$_2$N(CN)(SiR$^1$R$^2$R$^3$) is reacted with a compound represented by formula (14) Y$^{+-}$B, thus obtaining a compound represented by formula (12) Y$^+$[R$^f$SO$_2$NCN]$^-$. This is another example of a step that can be used to synthesize a compound represented by formula (12). This step (hereinafter sometimes referred to as 'step B5') can typically be represented by the following reaction formula.

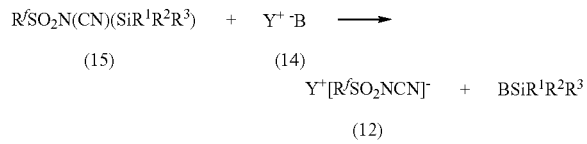

The compound represented by formula (15) used in the present step can, for example, be prepared using a method including step B1 described above. R$^f$ in formula (15) is any selected from perfluoroalkyl groups having 1 to 4 carbon atoms, and is the same as R$^f$ in the final target substance (i.e. the compound represented by formula (12)). R$^1$, R$^2$ and R$^3$ are each independently any selected from alkyl groups having 1 to 4 carbon atoms. As the compound represented by formula (14) used in the present step, a compound as Y$^{+-}$B described above in step B4 can be used.

It is generally appropriate for the amount used of the compound represented by formula (15) to be selected from within arrange of 0.5 to 1.5 mol per 1 mol of the Y$^{+-}$B. From a viewpoint of obtaining the target substance with a good yield, the amount used of the compound represented by formula (15) is preferably made to be within a range of 0.7 to 1.2 mol per 1 mol of the Y$^{+-}$B. From the viewpoint of economy, this amount is more preferably made to be within a range of 0.8 to 1.1 mol.

A solvent is not necessarily required in the reaction, but it is preferable to use a solvent so that the reaction can be carried out efficiently. As the solvent, a solvent as in step B4 described above can be used. Moreover, the reaction can be made to proceed at a reaction temperature as for step B4 described above.

<Ion-Conducting Material>

A composition comprising one or a plurality selected from salts between R$^f$STI or R$^f$SC and an organic cation may be an ion-conducting material exhibiting a liquid form in an ambient temperature range (e.g. 10 to 30° C., preferably 0 to 40° C., more preferably −20 to +60° C.). In one preferable embodiment of such a material, the material comprises at least one salt between R$^f$STI or R$^f$SC and an organic cation, the salt exhibiting a liquid form in a temperature range as above. An ion-conducting material disclosed here may comprise one or a plurality selected from salts between R$^f$STI or R$^f$SC and an inorganic cation (e.g. an alkali metal ion) instead of, or in addition to, the one or a plurality selected from salts between R$^f$STI or R$^f$SC and an organic cation.

In addition to the one or a plurality selected from salts between R$^f$STI or R$^f$SC and a cation, such an ion-conducting material may comprise another salt (i.e. a salt between an anion not categorized under either R$^f$STI or R$^f$SC and any of various organic cations or inorganic cations). As such 'another salt', for example the material may comprise a salt between an anion other than R$^f$STI or R$^f$SC and an organic cation, the salt exhibiting a liquid form in an ambient temperature range (i.e. being an ambient temperature molten salt).

In one preferable embodiment of the ion-conducting material disclosed here, the material is liquid in an ambient temperature range as described above in a state substantially not comprising components other than salts between R$^f$STI or R$^f$SC and a cation (e.g. organic solvents). Alternatively, the material is liquid in an ambient temperature range as described above in a state substantially not comprising components other than salts between R$^f$STI or R$^f$SC and a cation and other salts as described above (i.e. in a state substantially comprising only ionically bonded compounds). It may be that such an ion-conducting material can be suitably used as an electrolyte used in an electrical storage device such as any of various cells or capacitors or as a constituent of such an electrolyte. For example, such an ion-conducting material can be preferably used as a medium for dissolving a supporting electrolyte in an electrolyte used in an electrical storage device or the like (i.e. as a medium (solvent) for an electrolyte) instead of, or in addition to, conventional publicly known nonaqueous solvents.

<Electrolyte and Cell Containing Electrolyte>

[Electrolyte]

The ion-conducting material as described above comprising at least one salt between R$^f$STI or R$^f$SC and an organic cation, the salt exhibiting a liquid form in a temperature range as above, can be preferably used, for example, as an electrolyte in a cell that is charged and discharged through a cation passing between a positive electrode and a negative electrode, or as a constituent of such an electrolyte. For example, such a composition is suitable as an electrolyte in a cell in which the above cation is a lithium ion (typically a lithium ion secondary battery), or as a constituent of such an electrolyte. In addition to the one or a plurality selected from salts between R$^f$STI or R$^f$SC and an organic cation, the electrolyte used in such a cell may comprise a compound able to supply lithium ions to the electrolyte (a lithium source). As such a compound (also referred to as a 'supporting electrolyte' or 'supporting salt'), a lithium salt such as LiPF$_6$, LiBF$_4$, LiPF$_5$(CF$_3$), LiPF$_4$(CF$_3$)$_2$, LiPF$_4$(CF$_2$CF$_3$)$_2$, LiBF$_3$(CF$_3$), LiBF$_3$(C$_2$F$_5$), LiBF$_2$(CF$_3$)$_2$, LiBF(CF$_3$)$_3$, LiAsF$_6$, LiClO$_4$, LiSCN, LiOCOCF$_3$, LiCF$_3$SO$_3$, LiC$_4$F$_9$SO$_3$, LiN(SO$_2$C$_2$F$_5$)$_2$, LiC(SO$_2$CF$_3$)$_3$, LiOCOC$_6$F$_5$, LiN(SO$_2$CF$_3$)$_2$ (some times referred to as 'LiTFSI'), LiN(COCF$_3$)(SO$_2$CF$_3$) or LiN(COCF$_2$CF$_3$)(SO$_2$CF$_3$) can be selected.

In addition to the one or a plurality selected from salts between R$^f$STI or R$^f$SC and an organic cation, the electrolyte disclosed here may comprise one or a plurality selected from salts between R$^f$STI or R$^f$SC and a lithium cation. The electrolyte may comprise such a lithium salt as a supporting electrolyte.

In one preferable embodiment of the electrolyte disclosed here, such a lithium salt as a supporting electrolyte is dissolved in a liquid medium that is substantially constituted from one or a plurality selected from salts between R$^f$STI or R$^f$SC and an organic cation that exhibit a liquid form in a temperature range as above (ambient temperature molten salts). In another preferable embodiment of the electrolyte disclosed here, such a lithium salt as a supporting electrolyte is dissolved in a liquid medium that is substantially constituted from one or a plurality selected from ambient temperature molten salts between $R^fSTI$ or $R^fSC$ and an organic cation and other ambient temperature molten salts (i.e. ambient temperature molten salts having an anionic component other than $R^fSTI$ or $R^fSC$).

There are no particular limitations on the concentration of the supporting electrolyte. For example, a composition containing 0.1 to 20 mol of the supporting electrolyte (lithium salt) per 1 liter (L) of the electrolyte may be used. It is generally appropriate to make this supporting electrolyte content be in a range of 0.3 to 15 mol/L, with 0.5 to 10 mol/L being preferable. It is preferable to make the concentration be such that the supporting electrolyte can dissolve stably (i.e. without precipitation or the like being observed) at least in a temperature range of 10° C. and above (preferably 0° C. and above).

Moreover, the electrolyte may comprise general solvents (typically organic solvents). Examples of preferable solvents include aprotic solvents used in general lithium ion secondary battery electrolytes such as carbonates such as propylene carbonate (PC), ethylene carbonate (EC), dimethyl carbonate, diethyl carbonate (DEC) and ethyl methyl carbonate, cyclic esters such as γ-butyrolactone, other esters such as methyl acetate, ethyl acetate, methyl formate and ethyl formate, cyclic ethers such as tetrahydrofuran and 1,3-dioxolane, and ethers such as ethylene glycol dimethyl ether, ethylene glycol diethyl ether and diethylene glycol dimethyl ether. One or a plurality selected from such solvents may be contained in the electrolyte.

Although there are no particular limitations, with an electrolyte containing such a solvent, the solvent content is preferably made to be not more than the content of the salts between $R^fSTI$ or $R^fSC$ and an organic cation. That is, the electrolyte may be made to be such that the content of the solvent relative to 50 parts by mass of the salts between $R^fSTI$ or $R^fSC$ and an organic cation (the total amount in the case that a plurality of such salts are contained) is not more than 50 parts by mass (preferably not more than 15 parts by mass, more preferably not more than 5 parts by mass). An electrolyte in which salts between $R^fSTI$ or $R^fSC$ and an organic cation are made to constitute the principal component in this way is a preferable example of the electrolyte disclosed here.

The electrolyte disclosed here may be made to be a composition substantially comprising only ionically bonded compounds (salts). For example, the electrolyte may be a composition substantially constituted from one or a plurality selected from salts between $R^fSTI$ or $R^fSC$ and an organic cation, and a supporting electrolyte (e.g. a lithium salt). The electrolyte may further comprise ambient temperature molten salts other than salts between $R^fSTI$ or $R^fSC$ and an organic cation. An electrolyte that has such a composition and is liquid in an ambient temperature range (e.g. 10 to 30° C., preferably 0 to 40° C., more preferably −20 to +60° C.) is preferable. An electrolyte that can maintain a liquid state even at −30° C. is particularly preferable. A lithium ion secondary battery containing such an electrolyte can be suitably used at least in a temperature range of −30° C. and above (typically −30 to +100° C.). In particular, the lithium ion secondary battery may exhibit improved properties (ionic conductivity etc.) even in a temperature range below room temperature (e.g. below 25° C., and maybe below 0° C.).

[Other Constituent Elements of Cell]

A cell containing an electrolyte as described above may be constituted comprising a positive electrode having an active material for which absorption and release (e.g. insertion and extraction) of lithium ions can take place reversibly. As such a positive electrode active material, any of various lithium composite oxides containing at least lithium and a transition metal as constituent elements can be preferably used. Examples of such composite oxides include Li-Ni-containing oxides, Li-Mn-containing oxides and Li-Co-containing oxides. Here, 'Li-Ni-containing oxide' has a meaning encompassing not only oxides having Li and Ni as constituent elements, but also oxides containing at least one other metal element (i.e. at least one selected from transition metal elements and representative metal elements other than Li and Ni) in addition to Li and Ni. These metal elements may be one or a plurality selected from the group consisting of Co, Al, Mn, Cr, Fe, V, Mg, Ti, Zr, Nb, Mo, W, Cu, Zn, Ga, In, Sn, La and Ce. The same applies to 'Li-Mn-containing oxide' and 'Li-Co-containing oxide'.

The positive electrode of the cell disclosed here may have a constitution in which an positive electrode active material as described above is held on an electrically conductive member. A rod-like body, plate-like body, foil-like body, mesh-like body or the like having a metal such as aluminum (Al), nickel (Ni) or titanium (Ti) as a principal component thereof may be used as the electrically conductive member (collector). Alternatively, carbon paper or the like may be used. For example, a constitution in which a layer containing the active material (an active material-containing layer) is provided on the surface of a sheet-like electrically conductive member (e.g. Al foil) may be used. In addition to the active material, this active material-containing layer may as required contain one or a plurality of other materials generally used in positive electrodes. Examples of such materials include electrically conductive materials and binders. As electrically conductive materials, one or a plurality selected from carbon materials such as carbon black (acetylene black etc.), electrically conductive metal powders such as nickel powder, and so on can be used. As binders, one or a plurality selected from polyvinylidene fluoride (PVDF), polytetrafluoroethylene (PTFE), poly (vinylidene fluoride-hexafluoropropylene) copolymers (PVDF-HFP), styrene-butadiene block copolymers (SBR), carboxymethyl cellulose (CMC), and so on can be used.

The cell disclosed here may include a negative electrode having an active material for which absorption and release (e.g. insertion and extraction) of lithium ions can take place reversibly. As such a negative electrode active material, a carbon material having an amorphous structure and/or a graphite structure can be used. For example, one or a plurality selected from active materials generally used in lithium ion secondary battery negative electrodes such as natural graphite, mesocarbon microbeads (MCMBs), highly oriented pyrolytic graphite (HOPG), hard carbon and soft carbon can be preferably used. Alternatively, an oxide, a chalcogenide or the like can be used. For example, a lithium titanate (e.g. $Li_4Ti_5O_{12}$) can be preferably used as a negative electrode active material. The negative electrode may be made to have a constitution in which such an active material is held, together with binders and so on as required, on an electrically conductive member comprising a metal or the like. A rod-like body, plate-like body, foil-like body, mesh-like body or the like having a metal such as copper (Cu), aluminum (Al), nickel (Ni) or titanium (Ti) as a principal component thereof may be used as the electrically conductive member (collector). Alternatively, carbon paper or the like may be used. As binders, for example ones as for the positive electrode can be used. For example, a constitution in which a layer containing the active material (an active material-containing layer) is provided on the surface of a sheet-like electrically conductive member (e.g. Cu foil) may be used.

The cell disclosed here may be made to have a constitution in which an electrolyte as described above is disposed between such an positive electrode and negative electrode. Alternatively, the cell may be made to have a constitution in which a separator is disposed between the positive electrode and the negative electrode, and the electrolyte is soaked into the separator. As the separator, for example a porous film comprising a polyolefin resin such as polyethylene (PE) or polypropylene (PP) may be used. Moreover, a woven cloth or nonwoven cloth comprising polypropylene, polyethylene terephthalate (PET), methyl cellulose (MC) or the like may be used.

Moreover, the electrolyte disclosed here may be used as a solid electrolyte by carrying out molding (to form a film) of the electrolyte together with a supporting medium such as polyethylene oxide (PEO), an ethylene oxide-propylene oxide copolymer (EO-PO), polymethyl methacrylate (PMMA), polyvinylidene fluoride (PVdF) or a poly(vinylidene fluoride-hexafluoropropylene) copolymer (PVdF-HFP).

Following is a description of examples relating to the present invention; however, the present invention is not intended to be limited to these specific examples.

SYNTHESIS EXAMPLE 1

Synthesis of $CF_3SO_2N=CCl_2$ $$CF_3SO_2NCO + PCl_5 \rightarrow CF_3SO_2N=CCl_2 + POCl_3 \quad (S1)$$

$CF_3SO_2N=CCl_2$ was synthesized following the reaction formula (S1) above. Specifically, $CF_3SO_2NCO$ (52.8 g, 300 mmol) and $PCl_5$ (62.9 g, 300 mmol) were weighed out in a glove box into an autoclave having an inner tube made of polytetrafluoroethylene. The autoclave was sealed, and was then immersed in an oil bath; the temperature of the bath was raised to 180° C., and this temperature was held for 48 hours, thus making reaction proceed.

After the reaction was completed, the solid (unreacted $PCl_5$) was filtered off from the reaction liquid and was washed with pentane. Using a distillation apparatus equipped with a Vigreux column, the filtrate was distilled at normal pressure. $POCl_3$ produced through the above reaction was removed as a fore-running, and a fraction having a boiling point of 112 to 124° C. was obtained. The fraction obtained having a boiling point of 112 to 124° C. still contained a considerable amount of $POCl_3$, and hence this fraction was once again distilled at normal pressure, thus obtaining a fraction having a boiling point of 115 to 122° C. The product obtained in this way was a colorless transparent liquid. The yield was 27.3 g (39%).

Elemental analysis was carried out on the product obtained ($CF_3SO_2N=CCl_2$). The results are shown in Table 1. As can be seen from this table, the calculated values and the analytical values agree quite well.

TABLE 1

| | Element | | |
|---|---|---|---|
| | C | H | N |
| Calculated (mass %) | 10.44 | 0.00 | 6.09 |
| Observed (mass %) | 9.48 | 0.08 | 5.68 |

Furthermore, the product was dissolved in acetonitrile-$d_3$, and the $^{19}F$-NMR spectrum was measured taking $C_6F_6$ as a reference. Moreover, the IR spectrum was measured using a liquid film method (neat method). The spectral data obtained are shown in Table 2.

TABLE 2

| $^{19}F$-NMR(ppm) | IR(neat, cm$^{-1}$) |
|---|---|
| 85.15(s, CF$_3$) | 1645, 1609, 1586, 1398, 1231, 1131, 943, 825, 641, 587, 543, 510 |

A small amount of $POCl_3$ was detected in the product through the above IR spectrum measurements. The product obtained through the above step may be purified by distilling again to further remove this $POCl_3$.

SYNTHESIS EXAMPLE 2

Synthesis of $[CF_3SO_2NCF_3]^-Ag^+$ $$CF_3SO_2N=CCl_2 + AgF \rightarrow [CF_3SO_2NCF_3]^-Ag^+ + AgCl \quad (S2)$$

$[CF_3SO_2NCF_3]^-Ag^+$ was synthesized following the reaction formula (S2) above. Specifically, AgF (16.9 g, 133 mmol) and dry acetonitrile (40 mL) were weighed out into a 100 mL flask equipped with a tube of calcium chloride. The flask was immersed in an ice water bath, and while stirring the contents, a solution of the $CF_3SO_2N=CCl_2$ obtained in Synthesis Example 1 (8.49 g, 36.9 mmol) and dry acetonitrile (20 mL) was instilled in. As a result, an exothermic reaction took place. After this exothermic reaction had died down, the liquid reaction mixture was heated and refluxed for 2.5 hours. After the reaction was completed, the reaction liquid was allowed to cool down to room temperature, and then the AgCl (solid) produced was filtered off from the reaction liquid. The solvent was then distilled off from the filtrate. A large amount of diethyl ether was added to the residue thus obtained, and the insoluble component was filtered off. The solvent was then distilled off from the filtrate, and drying was carried out under reduced pressure at room temperature. In this way, 11.98 g of a liquid product was obtained. The yield was quantitative.

In addition to the target substance $[CF_3SO_2NCF_3]^-Ag^+$, the product contained $AgPF_6$, albeit in a small amount. It is surmised that this was produced through the AgF reacting with $POCl_3$ contained as an impurity in the $CF_3SO_2N=CCl_2$ used as a raw material. The $AgPF_6$ was removed using the following method. That is, 150 mL of diisopropyl ether was added to the product, thus dissolving the $[CF_3SO_2NCF_3]^-Ag^+$. The solution was left in a refrigerator (approximately 0 to 5° C.), and then the insoluble component was filtered off. The solvent was then distilled off from the filtrate, and thorough drying was carried out using a vacuum pump. In this way, it was possible to obtain the target substance ($[CF_3SO_2NCF_3]^-Ag^+$) in the form of a liquid containing only a trace amount of $AgPF_6$. The yield was 11.31 g (95%).

In the case that further purification is required, next the $[CF_3SO_2NCF_3]^-Ag^+$ obtained through the above step may be further purified through the reactions shown in formulae (S3) and (S4) below.

$$[CF_3SO_2NCF_3]^-Ag^+ + HCl \rightarrow CF_3SO_2NHCF_3 + AgCl\downarrow \quad (S3)$$

$$CF_3SO_2NHCF_3 + AgF \rightarrow [CF_3SO_2NCF_3]^-Ag^+ + HF \quad (S4)$$

Specifically, the $[CF_3SO_2NCF_3]^-Ag^+$ (30 mmol) obtained through the above step was put into a reaction vessel, and a stream of nitrogen gas was passed in, thus replacing the air inside the reaction vessel with nitrogen gas. The reaction vessel was then immersed in an ice water bath, dichloromethane (15 mL) was added, and the mixture was stirred, thus dissolving the $[CF_3SO_2NCF_3]^-Ag^+$. The stream of nitrogen gas was then stopped, and a sufficient amount (290 mmol here) of hydrogen chloride gas was passed in over 1.5 hours, thus bringing about reaction. Here, the hydrogen chloride gas was produced by adding NaCl to $H_2SO_4$.

After the reaction was completed, the AgCl (solid) produced was filtered off, and was washed with dichloromethane. The filtrate was then distilled at normal pressure, thus distilling off the dichloromethane, and then distillation under reduced pressure was carried out, thus obtaining a fraction having a boiling point of 65 to 66.5° C. at 73 mmHg. This fraction was once again distilled under reduced pressure, thus obtaining a fraction having a boiling point of 72 to 73° C. at 100 mmHg. The product ($CF_3SO_2NHCF_3$) obtained in this way was a colorless transparent liquid. The yield was 3.31 g (51%).

For the product ($CF_3SO_2NHCF_3$) obtained in this way, the $^{19}$F-NMR spectrum and the IR spectrum were measured as in Synthesis Example 1. Moreover, the product was dissolved in acetonitrile-d$_3$, and the $^1$H-NMR spectrum was measured taking $(CH_3)_4Si$ as a reference. The spectral data obtained are shown in Table 3. Note that 'q' in Table 3 means a quartet.

TABLE 3

| $^1$H-NMR(ppm) | $^{19}$F-NMR(ppm) | IR(neat, cm$^{-1}$) |
|---|---|---|
| 9.80(br.s., NH) | 110.86(q, J=4.0Hz, 3F, NCF$_3$), 85.80(q, J=4.0Hz, 3F, SCF$_3$) | 3282, 3078, 2866, 1463, 1415, 1279, 1179, 1140, 986, 851, 629, 603, 590, 506 |

Next, the $CF_3SO_2NHCF_3$ (2.17 g, 10 mmol) obtained through the above step was weighed out into a 30 mL polyethylene reaction vessel. Acetonitrile (2 mL) was then added, and the mixture was stirred at room temperature. AgF (1.27 g, 10 mmol) was then added, and the mixture was stirred for 1 hour. After that, to remove the HF produced, powdered NaF (2.10 g, 50 mmol) was added, and the mixture was stirred for 30 minutes. As a result, the HF was adsorbed onto the NaF. After that, diisopropyl ether (4 mL) was added, the solid component was filtered off, and then the filtrate was dried to a solid. The residue thus obtained was subjected to extraction with diisopropyl ether (10 mL). The resulting extract was subjected to filtration, and then the filtrate was dried to a solid. The residue thus obtained was dissolved in a small amount of acetonitrile, and then a large amount of hexane was added. The upper layer was removed, and then the lower layer was dried at room temperature under reduced pressure, thus obtaining the product ($[CF_3SO_2NCF_3]^-Ag^+$). This product was a colorless viscous liquid. The yield was 3.04 g (94%).

For the product ($[CF_3SO_2NCF_3]^-Ag^+$) obtained in this way, the $^{19}$F-NMR spectrum and the IR spectrum were measured as in Synthesis Example 1. The spectral data obtained are shown in Table 4.

TABLE 4

| $^{19}$F-NMR(ppm) | IR(neat, cm$^{-1}$) |
|---|---|
| 122.95(q, J=5.0Hz, 3F, SCF$_3$), 84.90(q, J=5.0Hz, 3F, NCF$_3$) | 1314, 1215, 1079, 1030, 803, 638, 611, 586, 512 |

SYNTHESIS EXAMPLE 3

Synthesis of Ionic Liquid (A1)

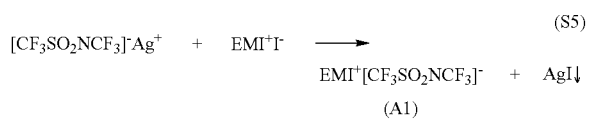

An ionic liquid substantially constituted from a salt having the structure shown in formula (A1) was obtained through the reaction formula (S5) above. 'EMI$^+$' in formula (A1) represents a 1-ethyl-3-methylimidazolium cation.

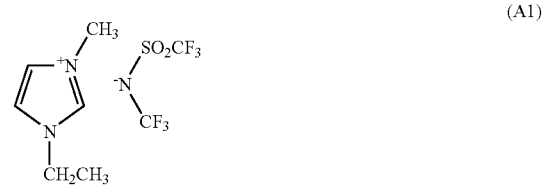

Acetonitrile (2 mL) was added to $[CF_3SO_2NCF_3]^-Ag^+$ (5.0 mmol) as a first compound, thus dissolving this first compound (the $[CF_3SO_2NCF_3]^-Ag^+$ obtained through Synthesis Example 2 was used as the first compound). A solution of 1-ethyl-3-methylimidazolium iodide (1.19 g, 5.0 mmol) as a second compound in acetonitrile (3 mL) was added, and the mixture was stirred for 10 minutes at room temperature. AgI produced through the reaction was filtered off from the reaction liquid, the solvent was distilled off from the filtrate, and drying was carried out under reduced pressure. Dichloromethane (10 mL) was added to the liquid residue remaining, thus dissolving this residue. The solution was washed with water, and anhydrous magnesium sulfate was added to the organic layer so as to dry the organic layer. The magnesium sulfate was then filtered off, approximately 0.2 g of activated charcoal was added to the filtrate and stirring was carried out for 1 minute, and then the activated charcoal was filtered off. The solvent was distilled off from the filtrate, and drying was carried out for 16 hours under reduced pressure at room temperature. The product obtained in this way was an almost colorless transparent viscous liquid (ionic liquid) at 25° C. The yield was 0.94 g (58%).

For the ionic liquid obtained, elemental analysis was carried out and the $^1$H-NMR spectrum, the $^{19}$F-NMR spectrum and the IR spectrum were measured as described above. The results are shown in Tables 5 and 6. The viscosity of the ionic liquid was measured using a falling ball viscosity measurement method. The result was that the viscosity at 25° C. was 29.7 mPa·s. The ionic liquid maintained a liquid state over a temperature range from at least room temperature (approximately 25° C. here) to −30° C.

TABLE 5

|  | Element | | |
|---|---|---|---|
|  | C | H | N |
| Calculated (mass %) | 29.36 | 3.39 | 12.84 |
| Observed (mass %) | 29.27 | 3.56 | 12.91 |

TABLE 6

| $^1$H-NMR(ppm) | $^{19}$F-NMR(ppm) | IR(neat, cm$^{-1}$) |
|---|---|---|
| 8.50(s, 1H, 2-H), 7.37(t, J=1.7Hz, 1H, 4- or 5-H), 7.32(t, J=1.7Hz, 1H, 4- or 5-H), 4.16(q, J=7.3Hz, 2H, CH$_2$), 3.82(s, 3H, NCH$_3$), 1.45(t, J=7.3Hz, 3H, CCH$_3$) | 123.46(q, J=4.6Hz, 3F, NCF$_3$), 84.52(q, J=4.6Hz, 3F, SCF$_3$) | 3160, 3122, 2993, 1575, 1472, 1317, 1215, 1171, 1125, 1072, 1028, 793, 636 |

SYNTHESIS EXAMPLE 4

Synthesis of Ionic Liquid (A2)

In the present synthesis example, 1-ethyl-2,3-dimethylimidazolium iodide was used as the second compound instead of the 1-ethyl-3-methylimidazolium iodide used in Synthesis Example 3. This second compound was reacted with an equimolar amount of [CF$_3$SO$_2$NCF$_3$]$^-$Ag$^+$ as in Synthesis Example 3, thus obtaining an ionic liquid substantially constituted from a salt having the structure shown in formula (A2) below. This ionic liquid was liquid at 25° C., and was also liquid at 20° C., and moreover even at 0° C.

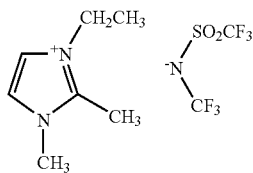

(A2)

For the ionic liquid obtained, the $^1$H-NMR spectrum, the $^{19}$F-NMR spectrum and the IR spectrum were measured as described above. The results are shown in Table 7.

TABLE 7

| $^1$H-NMR(ppm) | $^{19}$F-NMR(ppm) | IR(neat, cm$^{-1}$) |
|---|---|---|
| 7.27(d, J=2.2Hz, 1H, 4- or 5-H), 7.23(d, J=2.2Hz, 1H, 4- or 5-H), 4.08(q, J=7.3Hz, 2H, CH$_2$), 3.7(s, 3H, 3-CH$_3$), 2.5(S, 3H, 2-CH$_3$), 1.38(t, J=7.3Hz, 3H, CCH$_3$) | 123.53(q, J=4.7Hz, 3F, NCF$_3$), 84.58(q, J=4.7Hz, 3F, SCF$_3$) | 3150, 2992, 1591, 1542, 1393, 1316, 1215, 1173, 1120, 1069, 1027, 792, 635 |

SYNTHESIS EXAMPLE 5

Synthesis of Ionic Liquid (A3)

In the present synthesis example, tetrabutylammonium iodide was used as the second compound instead of the 1-ethyl-3-methylimidazolium iodide used in Synthesis Example 3. This second compound was reacted with an equimolar amount of [CF$_3$SO$_2$NCF$_3$]$^-$Ag$^+$ as in Synthesis Example 3, thus obtaining an ionic liquid substantially constituted from a salt having the structure shown in formula (A3) below. This ionic liquid was liquid at 25° C.

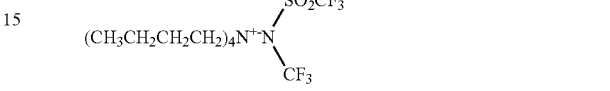

(A3)

For the ionic liquid obtained, the $^1$H-NMR spectrum and the $^{19}$F-NMR spectrum were measured as described above. The results are shown in Table 8.

TABLE 8

| $^1$H-NMR(ppm) | $^{19}$F-NMR(ppm) |
|---|---|
| 3.08(t, J=8.5Hz, 2H, NCH$_2$), 1.64-1.55(m, 2H, NCCH$_2$), 1.35(sextet, J=7.4Hz, 2H, NCCCH$_2$), 0.96(t, J=7.4Hz, 3H, CH$_3$) | 123.33(q, J=4.8Hz, 3F, NCF$_3$), 84.42(q, J=4.8Hz, 3F, SCF$_3$) |

SYNTHESIS EXAMPLE 6

Synthesis of CF$_3$CF$_2$SO$_2$N=CCl$_2$

Similar operations to in Synthesis Example 1 were carried out, but using CF$_3$CF$_2$SO$_2$NCO instead of the CF$_3$SO$_2$NCO in reaction formula (S1). As a result, CF$_3$CF$_2$SO$_2$N=CCl$_2$ (a liquid) was obtained as a fraction having a boiling point of 85 to 87° C. at 100 mmHg. The yield was 24%.

For the CF$_3$CF$_2$SO$_2$N=CCl$_2$ obtained, elemental analysis was carried out and the $^{19}$F-NMR spectrum and the IR spectrum were measured as described above. The results are shown in Tables 9 and 10.

TABLE 9

| | Element | | |
|---|---|---|---|
| | C | H | N |
| Calculated (mass %) | 12.87 | 0.00 | 5.00 |
| Observed (mass %) | 12.48 | <0.05 | 5.18 |

TABLE 10

| $^{19}$F-NMR(ppm) | IR(neat, cm$^{-1}$) |
|---|---|
| 85.19(s, 3F, CF$_3$), 46.80(s, 2F, CF$_2$) | 1603, 1401, 1329, 1235, 1195, 1140, 996, 941, 816, 756, 650, 568, 518 |

SYNTHESIS EXAMPLE 7

Synthesis of [CF$_3$CF$_2$SO$_2$NCF$_3$]$^-$Ag$^+$

Similar operations to in Synthesis Example 2 were carried out, but using the CF$_3$CF$_2$SO$_2$N=CCl$_2$ obtained in Synthesis Example 6 instead of the CF$_3$SO$_2$N=CCl$_2$ in reaction formula (S2). As a result, [CF$_3$CF$_2$SO$_2$NCF$_3$]$^-$Ag$^+$ (a solid) was obtained. The yield was 80%.

For the [CF$_3$CF$_2$SO$_2$NCF$_3$]$^-$Ag$^+$ obtained, the $^{19}$F-NMR spectrum was measured as described above. Moreover, the IR spectrum was measured using a KBr method. The results are shown in Table 11.

TABLE 11

| $^{19}$F-NMR(ppm) | IR(KBr, cm$^{-1}$) |
|---|---|
| 123.32(t, J=5.9Hz, 3F, NCF$_3$), 84.19(s, 3F, CCF$_3$), 45.95(q, J=5.9Hz, 2F, CF$_2$) | 1303, 1230, 1141, 1084, 1053, 981, 802, 655, 639 |

SYNTHESIS EXAMPLE 8

Synthesis of Ionic Liquid (A4)

Similar operations to in Synthesis Example 3 were carried out, but using the [CF$_3$CF$_2$SO$_2$NCF$_3$]$^-$Ag$^+$ obtained in Synthesis Example 7 as the first compound, and using an equimolar amount of 1-ethyl-3-methylimidazolium iodide as the second compound, thus obtaining an ionic liquid substantially constituted from a salt having the structure shown in formula (A4) below. The yield was 74%. This ionic liquid was liquid at 25° C., and maintained a liquid state over a temperature range from at least room temperature (approximately 25° C. here) to −30° C.

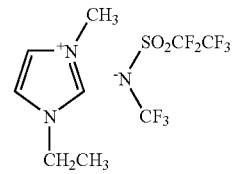

(A4)

For the ionic liquid obtained, elemental analysis was carried out and the $^1$H-NMR spectrum, the $^{19}$F-NMR spectrum and the IR spectrum were measured as described above. The results are shown in Tables 12 and 13.

TABLE 12

| | Element | | |
|---|---|---|---|
| | C | H | N |
| Calculated(mass %) | 28.65 | 2.94 | 11.14 |
| Observed(mass %) | 28.58 | 3.14 | 11.13 |

TABLE 13

| $^1$H-NMR(ppm) | $^{19}$F-NMR(ppm) | IR(neat, cm$^{-1}$) |
|---|---|---|
| 8.45(s, 1H, 2-H), 7.37(t, J=1.7Hz, 1H, 4- or 5-H), 7.32(t, J=1.7Hz, 1H, 4- or 5-H), 4.16(q, J=7.3Hz, 2H, CH$_2$), 3.81(s, 3H, NCH$_3$), 1.45(t, J=7.3Hz, 3H, CCH$_3$) | 123.59(t, J=5.9Hz, 3F, NCF$_3$), 84.12(s, 3F, CCF3), 45.61(q, J=5.9Hz, 2F, CF$_2$) | 3159, 3121, 1575, 1312, 1217, 1170, 1135, 1076, 1045, 976, 792, 752, 648, 633 |

SYNTHESIS EXAMPLE 9

Synthesis of CF$_3$SO$_2$N(CN)(Si(CH$_3$)$_3$)

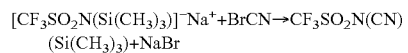

(S6)

CF$_3$SO$_2$N(CN)(Si(CH$_3$)$_3$) was synthesized following the reaction formula (S6) above. Specifically, [CF$_3$SO$_2$N(Si(CH$_3$)$_3$)]$^-$Na$^+$ (48.7 g, 200 mmol) and acetonitrile (80 mL) were weighed out into a 300 mL flask. The flask was immersed in an ice bath, and the contents were stirred. A solution of BrCN (21.2 g, 200 mmol) in acetonitrile (20 mL) was added, and the mixture was stirred for 10 minutes. After that, the flask was taken out from the ice bath, and the mixture was stirred for 1 hour at room temperature, and then the flask was immersed in a warm bath at 50° C., and the mixture was stirred for 16 hours. After that, the solid (NaBr) produced was filtered off. The solvent (CH$_3$CN) was distilled off from the filtrate at normal pressure, and then the residue was subjected to distillation under reduced pressure, thus obtaining a fraction having a boiling point of approximately 48° C. at 1 mmHg. This fraction was subjected to distillation under reduced pressure twice, thus obtaining a fraction having a boiling point of 60 to 64° C. at 2 mmHg as a very pale yellow liquid. The yield was 18.5 g (38%).

For the product obtained in this way [CF$_3$SO$_2$N(CN)(Si(CH$_3$)$_3$)], the $^{19}$F-NMR spectrum was measured as in Synthesis Example 1. Moreover, the $^1$H-NMR spectrum was measured in acetonitrile-d$_3$ taking (CH$_3$)$_4$Si as a reference.

The results obtained are shown in Table 14. From these spectral data, it is inferred that the product obtained in the present synthesis example was a mixture of three structural isomers in which $R^f$ in previously mentioned formulae (15a), (15b) and (15c) is $CF_3$, and each of $R^1$, $R^2$ and $R^3$ is $CH_3$.

TABLE 14

| $^{19}$F-NMR(ppm) | $^1$H-NMR(ppm) |
| --- | --- |
| 82.92(s, 0.37x3F, $CF_3$), | 0.30(s, 0.28x9H, $CH_3$), |
| 84.09(s, 0.36x3F, $CF_3$), | 0.38(s, 0.72x9H, $CH_3$) |
| 85.44(s, 0.27x3F, $CF_3$), | |

SYNTHESIS EXAMPLE 10

Synthesis of $[CF_3SO_2NCN]^-Ag^+$

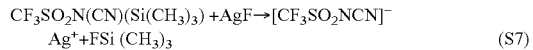
(S7)

$[CF_3SO_2NCN]^-Ag^+$ was synthesized through the reaction formula (S7) above using the $CF_3SO_2N(CN)(Si(CH_3)_3)$ obtained in Synthesis Example 9. Specifically, AgF (3.17 g, 25 mmol) and acetonitrile (6.5 mL) were weighed out into a 25 mL flask, the air in the flask was replaced with nitrogen gas, and then the flask was immersed in an ice bath and the contents were stirred. A solution of the $CF_3SO_2N(CN)(Si(CH_3)_3)$ (6.18 g, 25 mmol) in acetonitrile (6.5 mL) was added and the mixture was stirred for 5 minutes, and then the flask was taken out from the ice bath and the mixture was stirred for a further 30 minutes. After that, the insoluble component was filtered off from the reaction liquid. The solvent was then distilled off from the filtrate, and drying was carried out using a vacuum pump, thus obtaining $[CF_3SO_2NCN]^-Ag^+$ as a solid product. This product was purified as follows.

That is, the solid product was repeatedly subjected to extraction with diethyl ether, with the solvent then being distilled off from the extract and the extract then being dried under reduced pressure. The solid substance obtained after the drying was subjected to extraction with a 7/20 (volume ratio) mixture of diethyl ether/diisopropyl ether, and was then subjected to extraction with a 2/10 (volume ratio) mixture of diethyl ether/diisopropyl ether. The extracts were put together, the solvent was distilled off therefrom, and drying was carried out under reduced pressure. The solid substance obtained after the drying was washed well with diisopropyl ether, and was then dried under reduced pressure, thus obtaining high-purity $[CF_3SO_2NCN]^-Ag^+$ as the product, this being a pale gray solid. The yield was 5.62 g (80%).

For the $[CF_3SO_2NCN]^-Ag^+$ obtained in this way, the $^{19}$F-NMR spectrum was measured as described above. Moreover, the IR spectrum was measured using a KBr method. The results are shown in Table 15.

TABLE 15

| $^{19}$F-NMR(ppm) | IR(KBr, cm$^{-1}$) |
| --- | --- |
| 85.32(s, $CF_3$) | 2211, 1330, 1252, 1221, 1122, 844, 644, 599 |

SYNTHESIS EXAMPLE 11

Synthesis of $[CF_3SO_2NCN]^-Na^+$

(S8)

$[CF_3SO_2NCN]^-Na^+$ was synthesized through the reaction formula (S8) above. Specifically, $[CF_3SO_2NH]^-Na^+$ (3.42 g, 20 mmol), sodium carbonate (4.24 g, 40 mmol) and acetonitrile (40 mL) were weighed out into a 100 mL flask, the air inside the reaction vessel was replaced with nitrogen gas, and the reaction vessel was immersed in an ice bath. A solution of BrCN (2.34 g, 22 mmol) in acetonitrile (10 mL) was added while stirring, and then after stirring for 1 minutes, the flask was taken out from the ice bath, and stirring was carried out for 3 hours at room temperature. After the reaction was completed, the solid component was removed by filtration. The solvent was distilled off from the filtrate, and drying was carried out under reduced pressure, thus obtaining 4.00 g of a solid product. The yield was quantitative.

For the $[CF_3SO_2NCN]^{-Na+}$ obtained, the $^{19}$F-NMR spectrum and the IR spectrum were measured as described above; the data are shown in Table 16.

TABLE 16

| $^{19}$F-NMR(ppm) | IR(KBr, cm$^{-1}$) |
| --- | --- |
| 85.51(s, $CF_3$) | 2209(C≡N) |

SYNTHESIS EXAMPLE 12

Synthesis (1) of Ionic Liquid (B1)

$EMI^+[CF_3SO_2NCN]^-$ was synthesized through the reaction formula (S9) below using the $[CF_3SO_2NCN]^-Ag^+$ obtained in Synthesis Example 10.

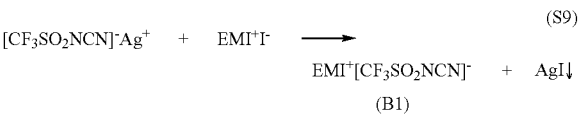
(S9)
(B1)

Specifically, the $[CF_3SO_2NCN]^-Ag^+$ (5.62 g, 20 mmol) and acetonitrile (10 mL) were weighed out into a 100 mL flask, a solution of 1-ethyl-3-methylimidazolium iodide (4.76 g, 20 mmol) in methylene chloride (40 mL) was added while stirring at room temperature, and the mixture was stirred for 30 minutes. After the reaction was completed, the solid (AgI) produced was filtered off. Water (3 mL) was added to the filtrate, and thorough mixing was carried out, and then the mixture was left to stand, and the upper aqueous layer was removed. This operation was repeated five times, and then anhydrous magnesium sulfate ($MgSO_4$) was added to the lower methylene chloride layer and stirring was carried out, and then after 5 minutes activated charcoal was added and stirring was carried out for 1 minute, before filtration was carried out. The solvent was distilled off from the filtrate, and drying was carried out under reduced pressure. A suitable amount of diisopropyl ether was added to the liquid obtained and the mixture was stirred vigorously, and then the mixture was left to stand, and the upper diisopropyl ether layer was removed. This operation was repeated three times, and then drying was carried out at room temperature under reduced pressure. In this way, a high-purity ionic liquid substantially constituted from a salt having the structure shown in formula (B1) below was obtained. The yield was 3.48 g (61%). This ionic liquid was liquid at 25° C.

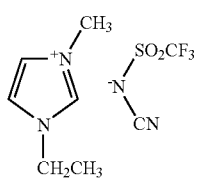
(B1)

For the ionic liquid obtained, elemental analysis was carried out and the $^1$H-NMR spectrum, the $^{19}$F-NMR spectrum and the IR spectrum were measured as described above. The results are shown in Tables 17 and 18. The viscosity of the ionic liquid was measured using a falling ball viscosity measurement method. The result was that the viscosity at 25° C. was 21.1 mPa·s. The ionic liquid maintained a liquid state over a temperature range from at least room temperature (approximately 25° C. here) to −30° C.

TABLE 17

|  | Element | | |
| --- | --- | --- | --- |
|  | C | H | N |
| Calculated(mass %) | 33.80 | 3.90 | 19.71 |
| Observed(mass %) | 33.79 | 3.98 | 19.79 |

TABLE 18

| $^1$H-NMR(ppm) | $^{19}$F-NMR(ppm) | IR(neat, cm$^{-1}$) |
| --- | --- | --- |
| 8.43(s, 1H, 2-H), 7.38(t, J=1.8Hz, 1H, 4- or 5-H), 7.33(t, J=1.8Hz, 1H, 4- or 5-H), 4.17(q, J=7.3Hz, 2H, CH$_2$), 3.82(s, 3H, 3-CH$_3$), 1.46(t, J=7.3Hz, 3H, CCH$_3$) | 85.45(s, CF$_3$) | 3158, 3118, 2991, 2192, 1575, 1470, 1332, 1216, 1170, 1120, 832, 753, 639, 595 |

SYNTHESIS EXAMPLE 13

Synthesis (2) of Ionic Liquid (B1)

In the present synthesis example, the ionic liquid (B1) was synthesized following the reaction formula (S10) below.

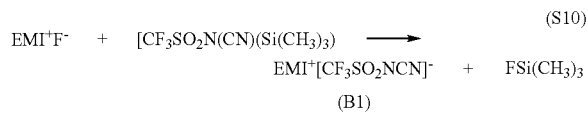
(S10)

The 1-ethyl-3-methylimidazolium fluoride (EMI$^+$F$^-$) used here was prepared as follows. That is, EMI$^+$I$^-$ (1.19 g, 5 mmol) and acetonitrile (10 mL) were weighed out into a 25 mL flask, AgF (0.63 g, 5 mmol) was added while stirring at room temperature, and then the stirring was continued for 30 minutes. The AgI precipitate produced was removed by filtration, thus preparing an acetonitrile solution of EMI$^+$F$^-$.

CF$_3$SO$_2$N(CN)(Si(CH$_3$)$_3$) (1.30 g, 5.25 mmol) was added to the acetonitrile solution of EMI$^+$F$^-$ at room temperature, and the mixture was stirred for 30 minutes. As the CF$_3$SO$_2$N(CN)(Si(CH$_3$)$_3$), that obtained through Synthesis Example 9 was used. After the reaction was completed, the reaction liquid was subjected to filtration, and then the solvent was distilled off from the filtrate, and drying was carried out under reduced pressure. The residue thus obtained was dissolved in ether, washed with water, and then treated with activated charcoal. After this treatment, the reaction liquid was dried under reduced pressure, thus obtaining an ionic liquid (B1). The yield was 1.40 g (83%). The ionic liquid (B1) obtained through the present synthesis example exhibited substantially the same spectral data as the ionic liquid (B11) synthesized in Synthesis Example 12.

SYNTHESIS EXAMPLE 14

Synthesis (3) of Ionic Liquid (B1)

In the present synthesis example, the ionic liquid (B1) was synthesized following the reaction formula (S11) below.

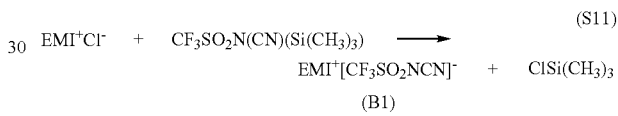
(S11)

1-ethyl-3-methylimidazolium chloride (EMI$^+$Cl$^-$) (0.73 g, 5 mmol) and methylene chloride (10 mL) were weighed out into a 25 mL flask. CF$_3$SO$_2$N(CN)(Si(CH$_3$)$_3$) (1.29 g, 5.25 mmol) was added, and the mixture was stirred for 30 minutes at room temperature. As the CF$_3$SO$_2$N(CN)(Si(CH$_3$)$_3$), that obtained through Synthesis Example 9 was used. After the reaction was completed, post-treatment was carried out as in Synthesis Example 13, thus obtaining an ionic liquid (B1). The yield was 1.48 g (88%). The ionic liquid (B1) obtained through the present synthesis example exhibited substantially the same spectral data as the ionic liquid (B 1) synthesized in Synthesis Example 12.

SYNTHESIS EXAMPLE 15

Synthesis of Ionic Liquid (B2)

In the present synthesis example, 1-ethyl-2,3-dimethylimidazolium iodide was used as the second compound instead of the 1-ethyl-3-methylimidazolium iodide used in Synthesis Example 12. Other than this, similar operations to in Synthesis Example 12 were carried out, thus obtaining an ionic liquid substantially constituted from a salt having the structure shown in formula (B2) below. The yield was 52%. This ionic liquid was liquid at 25° C.

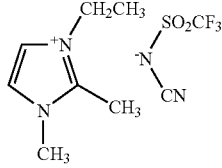

(B2)

For the ionic liquid obtained, elemental analysis was carried out and the $^1$H-NMR spectrum, the $^{19}$F-NMR spectrum and the IR spectrum were measured as described above. The results are shown in Tables 19 and 20. This ionic liquid maintained a liquid state over a temperature range from at least room temperature (approximately 25° C. here) to −30° C.

TABLE 19

|  | Element | | |
|---|---|---|---|
|  | C | H | N |
| Calculated(mass %) | 36.24 | 4.39 | 18.78 |
| Observed(mass %) | 36.00 | 4.44 | 18.79 |

TABLE 20

| $^1$H-NMR(ppm) | $^{19}$F-NMR(ppm) | IR(neat, cm$^{-1}$) |
|---|---|---|
| 7.27(d, J=2.2Hz, 1H, 4- or 5-H), 7.23(d, J=2.2Hz, 1H, 4- or 5-H), 4.08(q, J=7.2Hz, 2H, CH$_2$), 3.7(s, 3H, 3-CH$_3$), 2.5(S, 3H, 2-CH$_3$), 1.38(t, J=7.2Hz, 3H, CCH$_3$) | 85.68(s, CF$_3$) | 3149, 2990, 2191, 1591, 1542, 1455, 1332, 1234, 1217, 1180, 1120, 832, 753, 638, 596 |

SYNTHESIS EXAMPLE 16

Synthesis of Ionic Liquid (B3)

In the present synthesis example, 1,2-dimethyl-3-propylimidazolium iodide was used as the second compound instead of the 1-ethyl-3-methylimidazolium iodide used in Synthesis Example 12. Other than this, similar operations to in Synthesis Example 12 were carried out, thus obtaining an ionic liquid substantially constituted from a salt having the structure shown in formula (B3) below. The yield was 79%. This ionic liquid was liquid at 25° C.

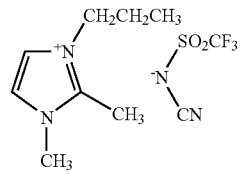

(B3)

For the ionic liquid obtained, elemental analysis was carried out and the $^1$H-NMR spectrum, the $^{19}$F-NMR spectrum and the IR spectrum were measured as described above. The results are shown in Tables 21 and 22. This ionic liquid maintained a liquid state over a temperature range from at least room temperature (approximately 25° C. here) to −30° C.

TABLE 21

|  | Element | | |
|---|---|---|---|
|  | C | H | N |
| Calculated (mass %) | 38.46 | 4.84 | 17.94 |
| Observed (mass %) | 38.19 | 4.90 | 17.60 |

TABLE 22

| $^1$H-NMR(ppm) | $^{19}$F-NMR(ppm) | IR(neat, cm$^{-1}$) |
|---|---|---|
| 7.25(d, J=2.2Hz, 1H, 4- or 5-H), 7.24(d, J=2.2Hz, 1H, 4- or 5-H), 4.00(t, J=7.3Hz, 2H, NCH$_2$), 3.69(s, 3H, 1-CH$_3$), 2.5(S, 3H, 2-CH$_3$), 1.79(sextet, J=7.3Hz, 2H, CCH$_2$), 0.93(t, J=7.3Hz, 3H, CCH$_3$) | 85.46(s, CF$_3$) | 3148, 2974, 2884, 2191, 1331, 1234, 1216, 1180, 1120, 831, 753, 637, 595 |

SYNTHESIS EXAMPLE 17

Synthesis (1) of Ionic Liquid (B4)

In the present synthesis example, N-methyl-N-propylpyrrolidinium iodide was used as the second compound instead of the 1-ethyl-3-methylimidazolium iodide used in Synthesis Example 12. Other than this, similar operations to in Synthesis Example 12 were carried out, thus obtaining an ionic liquid substantially constituted from a salt having the structure shown in formula (B4) below. The yield was 85%. This ionic liquid was liquid at 25° C.

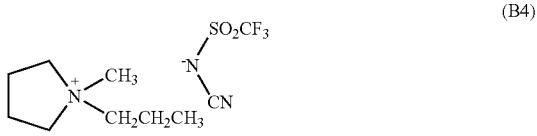

(B4)

For the ionic liquid obtained, the $^1$H-NMR spectrum, the $^{19}$F-NMR spectrum and the IR spectrum were measured as described above. The results are shown in Table 23.

TABLE 23

| $^1$H-NMR(ppm) | $^{19}$F-NMR(ppm) | IR(neat, cm$^{-1}$) |
|---|---|---|
| 3.47-3.36(m, 4H, 2-, 5-CH$_2$), 3.20(m, 2H, NCH$_2$), 2.95(s, 3H, NCH$_3$), 2.19-2.13(m, 4H, 3-, 4-CH$_2$), 1.82-1.71(m, 2H, NCCH$_2$), 0.96(t, J=7.1Hz, 3H, CCH$_3$) | 85.61(s, CF$_3$) | 2979, 2888, 2191, 1472, 1333, 1217, 1182, 1119, 832, 639, 596, 479 |

SYNTHESIS EXAMPLE 18

Synthesis (2) of Ionic Liquid (B4)

In the present synthesis example, the ionic liquid (B4) was synthesized following the reaction formula (S12) below using the [CF$_3$SO$_2$NCN]$^-$Na$^+$ obtained in Synthesis Example 1.

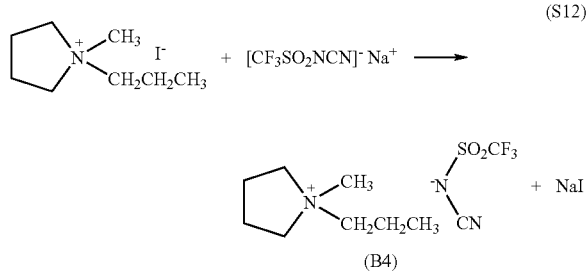

(S12)

(B4)

SYNTHESIS EXAMPLE 19

Synthesis of Ionic Liquid (B5)

In the present synthesis example, a salt between the cation represented by previously mentioned formula (22) and an iodide ion was used as the second compound instead of the N-methyl-N-propylpyrrolidinium iodide used in Synthesis Example 18. Other than this, similar operations to in Synthesis Example 18 were carried out, thus obtaining an ionic liquid substantially constituted from a salt having the structure shown in formula (B5) below. The yield was 63%. This ionic liquid was liquid at 25° C.

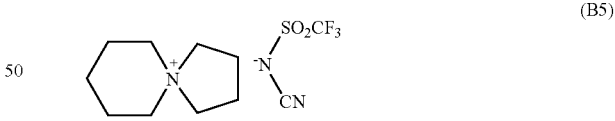

(B5)

For the ionic liquid obtained, the $^1$H-NMR spectrum, the $^{19}$F-NMR spectrum and the IR spectrum were measured as described above. The results are shown in Table 24.

N-methyl-N-propylpyrrolidinium iodide (1.28 g, 5 mmol) and acetonitrile (2 mL) were weighed out into a 25 mL flask. A solution of [CF$_3$SO$_2$NCN]$^-$Na$^+$ (0.98 g, 5 mmol) in acetonitrile (3 mL) was added while stirring at room temperature, and then the mixture was stirred for 10 minutes at room temperature. The reaction mixture was then subjected to filtration, and then the solvent was distilled off from the filtrate, and drying was carried out under reduced pressure. The residue thus obtained was dissolved in methylene chloride (10 mL), and the methylene chloride layer was repeatedly washed with water. After that, the solvent was distilled off from the methylene chloride layer, and drying was carried out under reduced pressure, thus obtaining an ionic liquid (B4). The yield was 0.49 g (33%). The ionic liquid (B4) obtained through the present synthesis example exhibited substantially the same spectral data as the ionic liquid (B4) synthesized in Synthesis Example 17.

TABLE 24

| $^1$H-NMR(ppm) | $^{19}$F-NMR(ppm) | IR(neat, cm$^{-1}$) |
|---|---|---|
| 3.45(t, J=7.2Hz, 4H, 1-, 4-CH$_2$), 3.28(t, J=5.9Hz, 4H, 6-, 10-CH$_2$), 2.15-2.09(m, 4H, 2-3-CH$_2$), 1.87-1.79(m, 4H, 7-, 9-CH$_2$), 1.64(quint, J=6.0Hz, 2H, 8-CH$_2$) | 85.60(s, CF$_3$) | 2955, 2191, 1466, 1332, 1215, 1180, 1119, 924, 831, 638, 595, 479 |

TEST EXAMPLE 1

Measurement of Ionic Conductivity

For the ionic liquids obtained through Synthesis Examples 3, 4, 12, 15 and 16, the ionic conductivity at 25° C. was measured. The measurement was carried out under an argon atmosphere with a conductivity meter, 'Model 3100' (a product of YSI/Nanotec. Inc.), using a '3417' probe (a product of YSI/Nanotec. Inc.) or an 'MI-915' or 'MI-905' (products of Microelectrodes, Inc.). The measurement results obtained are shown in Table 25 together with the structures of the salts constituting the ionic liquids.

TABLE 25

| Synthetic Example (salt) | cation | anion | ionic conductivity (mS/cm) (25° C.) |
|---|---|---|---|
| 3 (A1) | 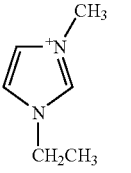 | 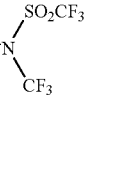 | 12.2 |
| 4 (A2) | 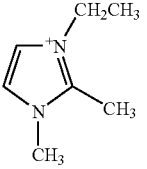 | 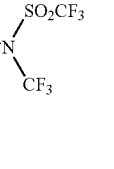 | 4.7 |
| 12 (B1) | 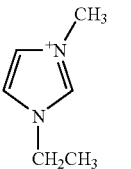 | 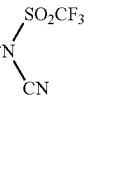 | 12.5 |
| 15 (B2) | 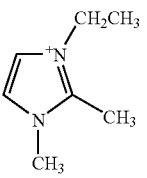 | 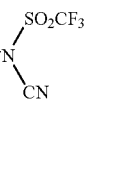 | 4.9 |
| 16 (B3) | 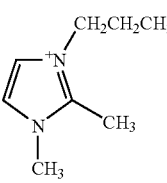 | 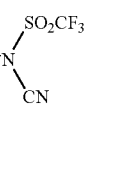 | 3.2 |

As can be seen from Table 25, each of the ionic liquids obtained through Synthesis Examples 3, 4, 12, 15 and 16 exhibited an ionic conductivity of over 3 mS/cm at 25° C. In particular, the ionic liquid (A1) substantially constituted from a 1-ethyl-3-methylimidazolium and the anion (TTI) represented by the formula $^-N(SO_2CF_3)(CF_3)$, and the ionic liquid (B1) substantially constituted from the same cation and the anion (TC) represented by the formula $^-N(SO_2CF_3)(CN)$ each exhibited an ionic conductivity of over 10 mS/cm (further over 12mS/cm) at 25° C.

TEST EXAMPLE 2

Temperature Dependence of Ionic Conductivity

For the ionic liquids obtained through Synthesis Examples 3 and 12, the ionic conductivity was measured as in Test Example 1 at measurement temperatures from −30 to +40° C. 1-ethyl-3-methylimidazolium bis(trifluoromethanesulfonyl) imide (hereinafter referred to as 'EMI-TFSI') and 1-ethyl-3-methylimidazolium 2,2,2-trifluoro-N-(trifluoromethanesulfonyl) acetamide (hereinafter referred to as 'EMI-TTA') are known as salts that have the same cation (1-ethyl-3-methylimidazolium) as the salts constituting the above ionic liquids and exhibit a liquid form in an ambient temperature range. The ionic conductivity was similarly measured at from −30 to +40° C. for ionic liquids constituted respectively from these salts. The results obtained are shown in FIG. 1. Moreover, the ionic conductivities of the ionic liquids at 25° C. are shown in Table 26 together with the structures of the salts constituting the ionic liquids.

TABLE 26

| Synthetic Example (salt) | cation | anion | ionic conductivity (mS/cm) (25° C.) |
|---|---|---|---|
| 3 (A1) | 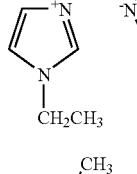 | 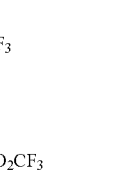 | 12.2 |
| 12 (B1) | 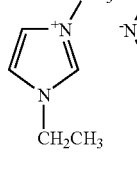 |  | 12.5 |
| EMI-TFSI | 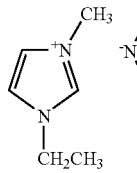 | 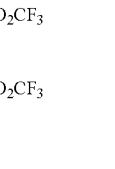 | 8 |
| EMI-TTA | 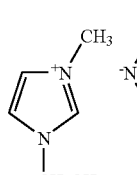 | 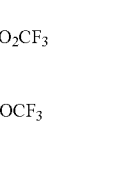 | 9 |

As can be seen from Table 26, the ionic liquids obtained through Synthesis Examples 3 and 12 each exhibited a good ionic conductivity at 25° C. that was 1.3 to 1.6 times higher than that of EMI-TFSI or EMI-TTA. Moreover, as can be seen from FIG. 1, the ionic liquids obtained through Synthesis Examples 3 and 12 each exhibited an ionic conductivity that was clearly better than that of either EMI-TFSI or EMI-TTA over a broad temperature range at least from +40° C. to −30° C. This ionic conductivity improvement effect tended to be more marked in a low-temperature region. A cell in which the ionic liquid obtained through Synthesis Example 3 or 12 is used as an electrolyte or a constituent thereof should thus function appropriately over a broad temperature range (particularly in a low-temperature region).

Specific examples of the present invention have been described in detail above; however these examples are merely illustrative, and do not restrict the scope of the claims. Any of various modifications of the specific examples illustrated above are included in the art described in the claims.

Moreover, the technical elements described in the present specification and drawings exhibit technical usefulness either alone or in any of various combinations, and there is no limitation to the combinations described in the claims at the time of filing. Moreover, the art illustrated in the present specification and drawings attains a plurality of objects simultaneously, but there is technical usefulness in attaining one of these objects.

What is claimed is:

1. A method of manufacturing a compound of formula (1):

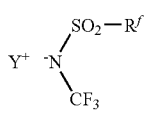
(1)

wherein $R^f$ is selected from perfluoroalkyl groups having 1 to 4 carbon atoms, and $Y^+$ is selected from organic and inorganic cations, wherein the organic cation is selected from an imidazolium ion, a thiazolium ion, an oxazolium ion, an iso-oxazolium ion, a triazolium ion, a pyridinium ion, a pyridazinium ion, a pyrimidinium ion, a pyrazinium ion, an ammonium ion, a phosphonium ion, and a sulfonium ion, wherein each of the foregoing is substituted or unsubstituted, and the inorganic cation is selected from a proton, an ammonium ion, a hydroxonium ion, a lithium cation, a sodium cation, a potassium cation, a rubidium cation, a cesium cation, a silver cation, a copper cation, and a gold cation;

the method comprising:
preparing a compound of formula (2):

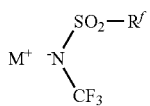
(2)

wherein $R^f$ is selected from perfluoroalkyl groups having 1 to 4 carbon atoms, and is the same as the perfluoroalkyl group selected in said formula (1), and $M^+$ is selected from alkali metal cations and a silver cation;

preparing a compound of formula (3):

$$Y^{+-}B \qquad (3)$$

wherein $Y^+$ is selected from organic and inorganic cations, wherein the organic cation is selected from an imidazolium ion, a thiazolium ion, an oxazolium ion, an iso-oxazolium ion, a triazolium ion, a pyridinium ion, a pyridazinium ion, a pyrimidinium ion, a pyrazinium ion, an ammonium ion, a phosphonium ion, and a sulfonium ion, wherein each of the foregoing is substituted or unsubstituted, and the inorganic cation is selected from a proton, an ammonium ion, a hydroxonium ion, a lithium cation, a sodium cation, a potassium cation, a rubidium cation, a cesium cation, a silver cation, a copper cation, and a cold cation, and $Y^+$ in said formula (3) is the same as $Y^+$ in said formula (1), and $^-B$ is selected from organic and inorganic anions; and then reacting said compound of formula (2) with said compound of formula (3) to produce said compound of formula (1).

2. The method according to claim 1, wherein M+ in said formula (2) is a silver cation.

3. The method according to claim 1, wherein $^-B$ in said formula (3) is a halide ion.

4. The method according to claim 1, wherein said compound of formula (2) is prepared by reacting a compound of formula (4):

$$R^fSO_2N{=}CX_2 \qquad (4)$$

wherein $R^f$ is selected from perfluoroalkyl groups having 1 to 4 carbon atoms, and is the same as the perfluoroalkyl group selected in said formula (2), and X is selected from halogen atoms;

with a metal fluoride of formula (5):

$$M^{+-}F \qquad (5)$$

wherein $M^+$ is selected from alkali metal cations and a silver cation, and is the same as $M^+$ selected in said formula (2).

5. The method according to claim 4, further comprising:
reacting said compound of formula (4) with said metal fluoride of formula (5) to obtain a compound of formula (2);
reacting the compound of formula (2) with acid to obtain a compound of formula (6):

(6)

wherein $R^f$ is selected from perfluoroalkyl groups having 1 to 4 carbon atoms, and is the same as the perfluoroalkyl group selected in said formula (2); and reacting said compound of formula (6) with said metal fluoride represented by said formula (5) to produce a compound of formula (2).

6. The method according to claim 4, wherein said metal fluoride of formula (5) is silver fluoride.

7. An ionic liquid comprising a compound of formula (8):

(8)

wherein $R^f$ is selected from perfluoroalkyl groups having 1 to 4 carbon atoms, and $Y^+$ is an organic cation selected from an imidazolium ion, a thiazolium ion, an oxazolium ion, an iso-oxazolium ion, a triazolium ion, a pyridinium ion, a pyridazinium ion, a pyrimidinium ion, a pyrazinium ion, an ammonium ion, a phosphonium ion, and a sulfonium ion, wherein each of the foregoing is substituted or unsubstituted.

8. The ionic liquid according to claim 7, wherein $R^f$ in said formula (8) is a trifluoromethyl group, and $Y^+$ in said formula (8) is a cation selected from 1-ethyl-3-methylimidazolium, 1-ethyl-2,3-dimethylimidazolium and tetrabutylammonium.

9. The ionic liquid according to claim 7, wherein $R^f$ in said formula (8) is a pentafluoroethyl group, and $Y^{30}$ in said formula (8) is a 1-ethyl-3-methylimidazolium cation.

* * * * *

UNITED STATES PATENT AND TRADEMARK OFFICE
CERTIFICATE OF CORRECTION

PATENT NO. : 7,541,492 B2  
APPLICATION NO. : 11/258214  
DATED : June 2, 2009  
INVENTOR(S) : Teruo Umemoto Page 1 of 1

It is certified that error appears in the above-identified patent and that said Letters Patent is hereby corrected as shown below:

Claim 9, col. 52, line 2, "$Y^{30}$" should read --$Y^+$--.

Signed and Sealed this

Eighteenth Day of August, 2009

David J. Kappos  
*Director of the United States Patent and Trademark Office*